United States Patent [19]

Tarcsay et al.

[11] 4,439,425
[45] Mar. 27, 1984

[54] PEPTIDE DERIVATIVES

[75] Inventors: Lajos Tarcsay, Grenzach-Wyhlen, Fed. Rep. of Germany; Bruno Kamber, Arlesheim, Switzerland; Jaroslav Stanek, Birsfelden, Switzerland; Gerhard Baschang, Bettingen, Switzerland; Albert Hartmann, Grenzach, Fed. Rep. of Germany

[73] Assignee: Ciba-Geigy Corporation, Ardsley, N.Y.

[21] Appl. No.: 385,594

[22] Filed: Jun. 7, 1982

Related U.S. Application Data

[63] Continuation of Ser. No. 225,277, Jan. 15, 1981, abandoned, which is a continuation of Ser. No. 104,246, Dec. 17, 1979, abandoned, which is a continuation-in-part of Ser. No. 53,573, Jun. 29, 1979, abandoned, which is a continuation-in-part of Ser. No. 915,699, Jun. 15, 9178, abandoned.

[30] Foreign Application Priority Data

Dec. 20, 1979 [CH] Switzerland ............... 12942/78

[51] Int. Cl.³ ............................................. A61K 37/00
[52] U.S. Cl. ............................................. 424/177
[58] Field of Search ................ 424/177; 260/112.5 R

[56] References Cited

FOREIGN PATENT DOCUMENTS

| 2279418 | 7/1975 | France ........................ 424/177 |
| 7206136 | 1/1973 | Netherlands ............... 424/177 |
| 7312987 | 3/1974 | Netherlands ............... 424/177 |
| 2347456 | 4/1974 | Switzerland ............... 424/177 |

OTHER PUBLICATIONS

Cellular Immunology 37, 174–187, (1978).
Infection and Immunity, (1978), 40–49, vol. 20.
Eur. J. Biochem. 34, (1973), 284–296.
Z. Immun-Forsch., vol. 153, 11–22, (1977).

*Primary Examiner*—Delbert R. Phillips
*Attorney, Agent, or Firm*—Irving N. Feit

[57] ABSTRACT

The present invention relates to new lipopeptides and in particular to compounds of either of the formulae

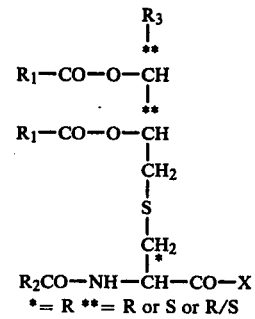

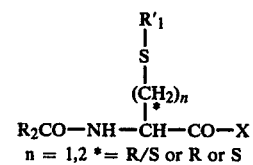

wherein $R_1$ and $R_2$ each represent a saturated or unsaturated aliphatic or mixed aliphatic-cycloaliphatic hydrocarbon radical which has 11–21 C atoms and which is also optionally substituted by oxygen functions, $R_3$ represents hydrogen or the radical $R_1$ —CO—O—CH$_2$—, where $R_1$ has the same meaning, $R_1'$ is a saturated or unsaturated aliphatic hydrocarbon radical of at least 9 C atoms, which is optionally substituted at one of the C atoms non adjacent to the sulfur atom by a free hydroxyl group or a hydroxyl group esterified with a monobasic carboxylic acid and which is optionally interrupted in the C atoms chain by one or more oxygen atoms, and which hydrocarbon is optionally substituted by a maximum of 2 cycloaliphatic hydrocarbon radicals having 5–8 ring C atoms, or $R_1'$ is the radical —CO—$R_1''$, wherein $R_1''$ represents a saturated or unsaturated aliphatic or mixed aliphatic-cycloaliphatic hydrocarbon radical of 11–21 C-atoms and which is optionally interrupted in the C atoms chain by oxygen atoms, and X represents an amino acid with free esterified or amidated carboxyl group, or an amino acid sequence of 2–10 aliphatic amino acids, the terminal carboxyl group of which is free or in the ester or amide form, the amino acids being naturals ones in the case of compounds of formula (1).

14 Claims, No Drawings

PEPTIDE DERIVATIVES

This is a continuation of application Ser. No. 225,277 filed on Jan. 15, 1981, which in turn is a continuation of application Ser. No. 104,246, filed Dec. 17, 1979, now abandoned, which is a continuation in part of Ser. No. 053,573, filed June 29, 1979, now abandoned, which is a continuation in part of Ser. No. 915,699, filed June 15, 1978, now abandoned.

The present invention relates to new lipopetides amnd in particular to compounds of either of the formulae

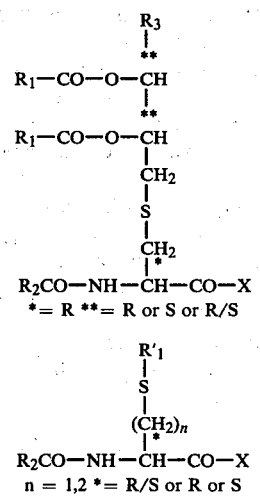

wherein $R_1$ and $R_2$ each represent a saturated or unsaturated aliphatic or mixed aliphatic-cycloaliphatic hydrocarbon radical which has 11–21 C atoms and which is also optionally substituted by oxygen functions, $R_3$ represents hydrogen or the radical $R_1$—CO—O—$CH_2$—, where $R_1$ has the same meaning, $R_1'$ is a saturated or unsaturated aliphatic hydrocarbon radical of at least 9 C atoms, which is optionally substituted at one of the C atoms non adjacent to the sulfur atom by a free hydroxyl group or a hydroxyl group esterified with a monobasic carboxylic acid and which is optionally interrupted in the C atoms chain by one or more oxygen atoms, and which hydrocarbon is optionally substituted by a maximum of 2 cycloaliphatic hydrocarbon radicals having 5–8 ring C atoms, or $R_1'$ is the radical —CO—$R_1''$, wherein $R_1''$ represents a saturated or unsaturated aliphatic or mixed aliphatic-cycloaliphatic hydrocarbon radical of 11–21 C-atoms and which is optionally interrupted in the C atoms chair by oxygen atoms, and X represents an amino acid with free, esterified or amidated carboxyl group, or an amino acid sequence of 2–10 aliphatic amino acids, the terminal carboxyl group of which is free or in the ester or amide form, the amino acids being naturals ones in the case of compounds of formula (I), and possibly to diastereomeric mixtures of these compounds, and salts and complexes, as well as to processes for the synthetic preparation of these compounds or mixtures, and to pharmaceutical preparations containing one or more of these lipopeptides together with a pharmaceutical carrier material. The above compounds have the R or S configuration of the C atoms indicated. The designation R/S indicates that the compounds of the above formulae according to the invention may be in the form of mixtures of compounds epimeric at the C atoms indicated by * and/or **.

Especially important are compounds fo formula (I') above which have the R configuration at the C* atom.

Lipopetides as degradation fragments of lipoproteins have already been described. Thus, e.g., Hantke and Braun (Eur. J. Biochem. 34, 284–296 (1973) were able to isolate from the murein lipoprotein of the outer cell wall of Escherichia coli, by enzymatic degradation, lipopeptide mixtures in impure form, to which may be attributed, in accordance with the examinations carried out, the following structure

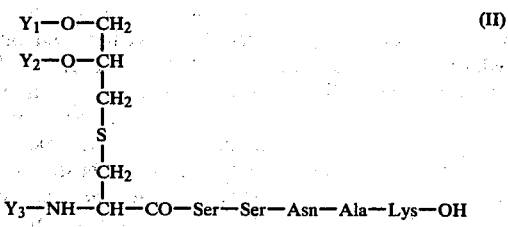

or corresponding formulae with shortened polypeptide chain, wherein $Y_1$, $Y_2$ and $Y_3$ represent acyl radicals of different higher saturated and unsaturated fatty acids, for instance of those having 14–19 C atoms and of others. Also the murein protein as such is based on the same structure (loc.cit). Both murein lipoprotein and its stated degradation products exhibit in vitro mitogenic activity towards some lymphocytes [see also Z. Immun.-Forschung, Vol. 153, pp. 11–22 (1977)].

As can be seen, the degradation lipopeptides obtained from murein protein are based on "glycerylcysteine"

As products of an enzymatic cleavage of natural products, these fragments were not products well defined in their composition, and were obviously complex mixtures of condensation products of the stated peptide part and very different acyl derivatives of glycerylcysteine.

The lipoptides of the present application differ from the stated degradation products of murein proteins in many respects: they are lipopetides of a precisely defined unitary chemical constitution and configuration, which are obtainable synthetically, and which are therefore suitable for therapeutic application. Moreover, the amino acids sequence can be different from that indicated above for the known degradation lipopetides mixtures in the formula (II), or in place thereof there is just a single amino acid. The glycerol part of the "glycerylcysteine" moiety may be replaced in the compounds of the present invention by different residues, e.g. by an erythrite residue in the compounds of formula (I) and by higher hydrocarbon radicals optionally containing ether groups and which can optionally be substituted at most by one free or esterified hydroxyl group and/or by higher alicyclic hydrocarbon radicals in case of compounds of formula (I'). Finally, amides and esters of the terminal carboxyl groups are also encompassed by the new compounds.

Whereas the configuration at the cysteine in the known mixtures of lipopeptides is only R, it can be also S in the compounds of formula (I') according to the present invention.

In the acyl group $R_2CO$ in the compounds of formula I and derivatives thereof, is a saturated or unsaturated, aliphatic or aliphatic-cycloaliphatic hydrocarbon radical which is also optionally substituted by oxygen functions and which has 11–21 C atoms, i.e. the acyl groups is derived from saturated or unsaturated, aliphatic or cycloaliphatic-aliphatic carboxylic acids which are optionally oxygenated in the hydrocarbon radical and which contain 12–22, preferably 14–18, C atoms. To be mentioned as such are the saturated or unsaturated fatty acids, such as lauric acid, myristic acid, palmitic acid, margaric acid, stearic acid, arachic acid, oleic acid, elaidic acid, linoleic acid, α- and β-eleostearic acid, stearolic acid or α-linolenic acid; and among the cycloaliphatic-aliphatic acids, e.g.: dihydrosterculic acid, malvalic acid, hydnocarpic acid and chaulmoogric acid. Oxygenated acids of this type, which are likewise suitable for the acyl group $R_2CO$, are, e.g., the acids obtained by epoxidation of the above-mentioned olefinic fatty acids and cycloaliphatic-aliphatic acids, e.g. γ,L-epoxystearic acid, also derivatives of the above-mentioned acids, which contain, e.g., one or more hydroxyl groups, such as ricinoleic acid.

The peptide sequence X in the compounds of formulae (I) and (I') or their salts consists of a maximum of 10 amino acids, preferentially with at least half carrying a hydrophilic group, such as in particular hydroxyl, amino, carboxyl, carbamide, guanidino or imidazolyl groups. Of the ionic amino acids of this category there may be singeled out among others those carrying acid groups, in particular aspartic acid and glutamic acid and oxyglutamic acid, and among those carrying basic groups especially lysine, ornithine, arginine and histidine. Amino acids having neutral character are in particular the amides, such as asparagine and glutamine, and those carrying hydroxyl groups are above all serine and threonine.

If X in the formulae (I) and (I') represents the amino acid mentioned, it is likewise one of the specified amino acids, e.g. one carrying hydrophilic groups, e.g. especially serine or threonine.

Among the amino acids which can go into the above sequence and which carry no hydrophilic groups, there are to be mentioned in particular the unsubstituted amino acids, such as glycine, alanine, valine, norvaline, leucine, isoleucine and phenylalanine; also, however, some substituted amino acids which are of non-hydrophilic character, such as methionine, are of interest.

The sequence of the stated amino acids in the peptide chain X can be optional, but preferred sequences are those in which all the amino acids having hydrophilic groups are bound directly to each other, and among such are preferred those in which this sequence of hydrophilic amino acids is bound to the carboxyl group of the substituted cysteine or homo-cysteine part.

The amino acid X or the sequence of amino acids X can also be any D- or L-amino acids in case of the compounds of formula (I'). The designation "aliphatic amino acids" in the above definition means any amino acid whose amino and carboxyl groups are each bonded to an aliphatic C atom, that is to say one which is no part of an aromatic system. Also in the case of compounds of the formula (I') a preferred group is that in which the amino acids are "natural" ones.

The hydrocarbon radical $R_1'$ in formula (I') is preferably of the formula

wherein $R_3'$ represent a saturated or unsaturated unsubstituted aliphatic hydrocarbon radical with at least 12 C atoms, or such hydrocarbon radical which is substituted by at most one free hydroxyl group or a hydroxyl group esterified with a monobasic carboxylic acid, which hydrocarbon radicals can optionally be interrupted in the carbon atoms chain by one or more oxygen atoms and/or substituted by at most 2 cycloaliphatic hydrocarbons radicals having 5–8 ring C atoms.

The mentioned aliphatic hydrocarbon radicals $R_1'$ and $R_3'$ and the derivatives containing oxygen functions and/or cycloaliphatic hydrocarbon radicals can be saturated or unsaturated, straight lined or branched, and they possess preferably a total of not more than 60 C atoms. Among the branched radicals those are preferred, in which at least one straight chain with 12–24 C atoms is present, which may be substituted by further shorter chains. In the unsaturated radicals there may be present several isolated and/or conjugated double bonds, especially up to 2 for each straight chain, preferably 2 conjugated double bonds. The said aliphatic hydrocarbon radicals are preferably alkyl, alkenyl or alkadienyl radicals with the mentioned preferred constitution and/or the said number of C atoms. Alkyl radicals $R_1'$ are e.g. n-dodecyl, n-tridecyl, n-tetradecyl, n-pentadecyl, n-hexadecyl, n-heneicosyl and n-docosyl or radicals derived therefrom by being substituted at one or more non terminal C atoms by methyl or ethyl radicals. Alkenyl radicals $R_1'$ are derived e.g. from the said alkyl radicals and they are e.g. 11-dodecenyl, 13-tetradecenyl, 14-pentadecenyl, 15-hexadecenyl, 16-heptadecenyl, 17-octadecenyl, 18-nonadecenyl, 20-eicosenyl or one of their isomers with the double bond in another position, such as for instance 9-octadecenyl, 8-docosenyl, or especially the alkenyl radical derived from phytol, the 3,7,11,15-tetramethyl-2-hexadecenyl. Among the radicals with several double bonds there should be mentioned the alkatrienyl radical derived from farnesol, that is to say the 3,7,11-trimethyl-2,6,10-dodecatrienyl. A hydrocarbon radical $R_1'$, such as one of those mentioned, can also be substituted by at most 2 cycloaliphatic hydrocarbon radicals, which have rings with 5–8 C atoms, and which are unsubstituted or are substituted by lower alkyl radicals with 1–7 C atoms, especially methyl groups. Such alicyclic rings are primarily cyclohexyl rings or their unsaturated derivatives, such as cyclohexenyl or cyclohexadienyl. As a particular example of these mixed aliphatic-cycloaliphatic radicals there is to be mentioned the 3,7-dimethyl-9-(2,6,6-trimethyl-1-cyclohexenyl)-2,4,7,8-nona-tetraenyl.

A hydrocarbon radical $R_3'$ can also be one of these alkyl, alkenyl or alkapolyenyl radicals. An alkyl radical $R_3$ is primarily one of the formula

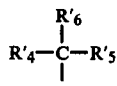   (V)

   (VI)

in which at least one of the substituents R$_4'$, R$_5'$, R$_6'$ represents alkyl, alkenyl or alkadienyl with a straight chain of 12-24 C atoms, it being optionally substituted by methyl or ethyl groups, while the others may be hydrogen or lower alkyl or alkenyl radicals with 1-7 C atoms, such as, in particular, methyl, ethyl, propyl, butyl, isopropyl, n-hexyl or n-heptyl. Also in this case the long chain alkyl, alkenyl or alkapolyenyl radicals can be those mentioned above as being preferred ones.

The radical R$_1'$ can, moreover, be the 5-cholen-3-yl-radical, that is to say, the residue of cholesterol, which is bound by its 3-position to the sulfur atom of the cysteine moiety in the compounds of the formula (I).

The hydrocarbon radicals R$_1'$ and R$_3'$ mentioned can also be interrupted in the C atoms chain by oxygen atoms. They are in this case ether radicals, there being present optionally one or more —O—groups, such groups being separated in the latter case mentioned by a chain of at least 2 C atoms. The preferred ether groups are also derived from the hydrocarbon radicals pointed out above. Thus, for instance, polyethyleneglycol radicals having the same number of C atoms as the alkyl groups mentioned above can be present.

Also in the case of the ethers, compounds of the above formula (V) are preferred in which the ether groups are present in the long chain alkyl, alkenyl or alkapolyenyl radicals and/or in one of the lower alkyl or alkenyl radicals or 1-7 C atoms mentioned. Preferably —O—groups in a long chain radical R$_4'$, R$_5'$ or R$_6'$ are adjacent to the central C atom indicated in formula (V), and there is preferably present at most one —O—group in each of such radicals.

In the said lower alkyl or alkenyl radicals the ether groups are preferably present at the free end of the carbon atoms-chain, especially in the form of methoxy groups. The radical R$_1'$ in formula (I') can also represent a group —CO—R$_1''$, wherein R$_1''$ means a saturated or unsaturated, aliphatic or mixed aliphtic-cycloaliphatic hydrocarbon radical of 11-21 C atoms. This radical can especially be one of one of the radicals set forth for formulae (IV) or (V), the number of the carbon atoms being, however, at most 21. The preferred radicals are also those especially singled out above for the groups of formula (IV) and (V). These radicals can also be interrupted in the C atoms chain by —O— groups, and the ether groups so formed can again be any of those especially mentioned above.

A radical R$_1''$ can, however, also be one of the radicals according to formulae (VIII) and (IX) reported below.

An important group [Group I] of lipopeptides according to formula I above is formed by those in which the peptide chain consists of a maximum of 5 amino acids. To be mentioned among these are in particular the lipopeptides of the formula wherein R$_1$ and R$_2$ have the same meanings, and X has the meaning given under the formula (I), but contains 2-5 amino acids in the case of the amino acid sequence, in which, preferably, at least half carry a hydrophilic group, and also the salts and complexes thereof. Among these lipopeptides, there may be emphasised those of which the amino acid sequence in the group X corresponds to that of the aforementioned lipopeptides obtained by degradation of murein lipoprotein, i.e. corresponds to that of the formula (II), or to a shortened chain derived therefrom. There may be mentioned in particular the following lipopetide types:

(AcGCT-acyl-glycerylcysteine part according to the formula (VI):
AcGCT-Ser-Ser-Asn-Ala-Lys-OH
AcGCT-Ser-Ser-Asn-Ala-OH
AcGCT-Ser-Ser-Asn-OH
AcGCT-Ser-Ser-OH;
also the corresponding types in which threonine, glutamine or asparagine replace serine; furthermore the compound types of the following kind:
AcGCT-Ser-Ser-Asn-Ala-Glu-OH
AcGCT-Ser-Ser-Phe-Ala-Glu-OH
AcGCT-Ser-Ser-Phe-Ala-OH
AcGCT-Ser-Ser-Phe-OH,
and the corresponding compounds with threonine, glutamine or asparagine as exchange amino acids for serine, and the amides and carboxylic acid esters having a terminal carbamide or ester group, with particular consideration being given to compounds in which the acyl groups R$_1$—CO, R$_2$—CO in the acylglycerylcysteine part are identical and are palmitoyl, stearoyl or oleoyl, and to all those compounds in which R$_1$—CO and R$_2$—CO are different and are, e.g., palmitoyl, stearoyl or oleoyl, and in which these radicals occur in any chosen combination and/or variation, such as those listed in the following Table, wherein the glycerylcysteine part corresponding to the N— and O—acyl substituents is written in abbreviated form as N-acyl-O-O-di-acyl-cys:

N—palmitoyl-O,O—di-palmitoyl-cys-Ser—Ser—Asn—Ala—Lys—OH
N—palmitoyl-O,O—di-palmitoyl-cys-Ser—Ser—Asn—Ala—OH
N—palmitoyl-O,O—di-palmitoyl-cys-Ser—Ser—Asn—OH
N—palmitoyl-O,O—di-palmitoyl-cys-Ser—Ser—OH
N—palmitoyl-O,O—di-palmitoyl-cys-Ser—OH
N—stearoyl-O,O—di-stearoyl-cys-Ser—Ser—Asn—Ala—Lys—OH
N—stearoyl-O,O—di-stearoyl-cys-Ser—Ser—Asn—Ala—OH
N—stearoyl-O,O—di-stearoyl-cys-Ser—Ser—Asn—OH
N—stearoyl-O,O—di-stearoyl-cys-Ser—Ser—OH
N—stearoyl-O,O—di-stearoyl-cys-Ser—OH
N—oleoyl-O,O—di-oleoyl-cys-Ser—Ser—Asn—Ala—Lys—OH
N—oleoyl-O,O—di-oleoyl-cys-Ser—Ser—Asn—Ala—OH
N—oleoyl-O,O—di-oleoyl-cys-Ser—Ser—Asn—OH
N—oleoyl-O,O—di-oleoyl-cys-Ser—Ser—OH
N—oleoyl-O,O—di-oleoyl-cys-Ser—OH
N—lauroyl-O,O—di-lauroyl-cys-Ser—Ser—Asn—Ala—Lys—OH
N—lauroyl-O,O—di-lauroyl-cys-Ser—Ser—Asn—Ala—OH -continued N—lauroyl-O.O—di-lauroyl-cys-Ser—Ser—Asn—OH
N—lauroyl-O.O—di-lauroyl-cys-Ser—Ser—OH
N—lauroyl-O.O—di-lauroyl-cys-Ser—OH;

and in addition compounds resulting from the substitution of serine by threonine, glutamic acid, glutamine, aspartic acid or asparagin, from the substitution of lysine by glutamic acid, and compounds resulting from the simultaneous substitution of lysine by glutamic acid and asparagine by phenylalanine.

Among the compounds having different acyl groups on N and O atoms in the glycerylcysteine part, the following are to be emphasised:

N—myristoyl-O.O—di-palmitoyl-
    Cys—Phe—Phe—Asn—Ala—Lys—OH
N—lauroyl-O.O—di-palmitoyl-
    Cys—Ser—Ser—Asn—Ala—Glu—OH
N—stearoyl-O.O—di-palmitoyl-
    Cys—Ser—Ser—Asn—Ala—Ala—OH, and the compounds resulting from replacement of Ser by Phe or of Phe by Ser.

A second group of compounds [Group II] according to the invention are compounds corresponding to the above formula IV in which however the configuration on the C** atom is S instead of R, and the mixtures of R- and S-diastereoisomers, such as can occur, for example, in the synthetic process of preparation. Specific types and compounds correspond in this group too to those particularly emphasised in the foregoing for the "R" group (formula VI).

A third [Group III] of the new lipopeptides comprises the compounds according to the formula (VI) in which however X represents an amino acid sequence having 6–10 amino acids, with the first 5 preferably constituting the sequence already emphasised above. The amino acids 6–10 can be any of the natural amino acids mentioned above, such as in particular serine, asparagine, alanine, glutamic acid, lysine or phenylalanine, and can occur for instance in the following sequences:
Ile-Asp-Glu-OH and
Asp-Glu-OH.

Specific compounds are, e.g.:
N-stearoyl-S-[2(R),3-dipalmitoyloxypropyl]-Cys-Ser-Ser-Asn-Ala-Glu-Ile-Asp-Glu-OH,
N-palmitoyl-S-[2-(R),3-dipalmitoyloxypropyl]-Cys-Ser-Ser-Asn-Ala-Glu-Ile-Asp-Glu-OH, and
N-palmitoyl-S-[2(R),3-dipalmitoyloxypropyl]-Cys-Ser-Ser-Asn-Ala-Lys-Ile-Asp-Glu-OH.

It is possible according to the invention to also produce corresponding compounds of this type with the S-configuration on the C** atom, as well as diastereoisomeric mixtures of S- and R-compounds.

A fourth group [Group IV] of lipopeptides according to the invention comprises compounds of the formula (I) in which $R_3$ represents the radical $R_1$—CO—O—$CH_2$—, wherein the configuration on the C** atoms is R or S, particularly also diastereoisomeric mixtures. Subgroups are compounds of the formula

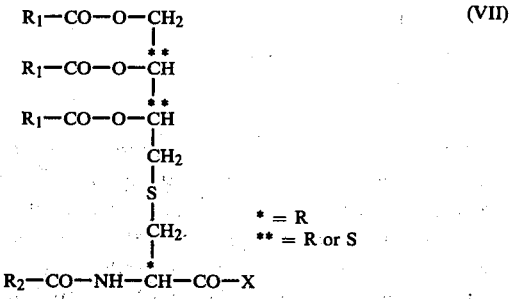

(VII)

especially those having the R-configuration on the C** atoms, wherein X has the meaning given under the formula (VI). The acyl groups $R_1$—CO— and $R_2$—CO— are preferably the same and are preferably again palmitoyl, stearoyl or oleoyl; they can be however, in the way discussed in the foregoing with regard to the other groups, in all combinations and/or variations. Preferred types and compounds of this class are again those in which X has the meanings specified above. For this group too, X is preferably an amino acid or a sequence of 5 amino acids, particularly one of those designated above as being preferred in the case of the other three groups of lipopeptides. X can however also represent one of the amino acid sequences with 6–10 amino acids described for the third group of lipopeptides of the present application, particularly the sequences specifically mentioned for that group.

Specific compounds are, e.g., those derived from the above Table compiled for specific compounds of the Group I if, in these compounds, N-acyl-O-O-di-acyl-cys does not denote as in that case the glycerylcysteine part but the erythritylcysteine part; and the compounds resulting from substitution of serine by threonine, glutamic acid, glutamine, aspartic acid or asparagine, and of lysine by glutamic acid, and, optionally, simultaneously of Asn by phenylalanine.

A fifth group of lipopeptides according to the present invention is formed of those compounds according to the formula (I) in which X represents a peptide chain wherein the sequence of the first 5 amino acids is different from those present in the known murein-lipoprotein-degradation lipopeptides, and particularly of such compounds wherein $R_3$ represents hydrogen, which correspond therefore to the above formula (VI), where $R_1$—CO and $R_2$—CO represent the acyl groups particularly emphasised as being preferred in the foregoing and in the following, in the stated combination, and also of salts and complexes thereof. There may be mentioned for example the following lipopeptide types
(AcGCT=acyl—glycerylcysteine part according to the formula (IV))
AcGCT-Phe-Ile-Ile-Phe-Ala-OH
AcGCT-Val-Lys-Val-Try-Pro-OH
and amides and esters thereof, particularly those especially emphasised in the following.

A further subgroup comprises compounds according to the formula (VI) in which X represents however the said "unnatural" sequence of amino acids in comparison with the murein-lipoprotein degradation products, and in which 6–10 amino acids are present. The first five amino acids have e.g. the sequence given above or any other desired sequence; there may be mentioned, e.g., the following lipopetides, where AcGCT has the above meaning:

AcGCT-Ala-Ile-Gly-Val-Gly-Ala-Pro-OH
AcGCT-Ser-Ser-Asn-Ala-Glu-Ile-Asp-Glu-OH
and amides and esters thereof, particularly those emphasised in the following.

There are preferably produced compounds of this type in which the configuration on the C** atom of the AcGCT is R, or mixtures of R- and S-epimers.

Preferred compounds of formula (I') and their derivatives are those in which the radical $R_1'$ has the following formula

wherein $X_1$ and $X_2$ each represent alkyl or alkenyl with 12–20 C atoms, $R_7'$ is hydrogen or alkyl or alkenyl with 12–20 C atoms or the radical $-CH_2-O-X_3$, where $X_3$ represents alkyl or alkenyl with 12–20 C atoms, the alkyl or alkenyl groups being preferably any of the groups singled out above.

There are of particular interest among the compounds of this group those wherein $R_7'$ is hydrogen or the radical $-CH_2-O-X_3$ mentioned. The alkyl or alkenyl groups $X_1$, $X_2$ and $X_3$ can be identical or different. Preferred are compounds in which the groups $X_1$, $X_2$ or all three groups $X_1$, $X_2$ and $X_3$ are identical and represent preferably hexadecyl, octadecyl or docosanyl. In one or more or the above radicals $X_1$, $X_2$, $X_3$ there can also be a further $-O-$group, especially so as to from a terminal methoxy or alkoxy group in these radicals.

Another preferred group of ethers, which can represent the radical $R_3'$ in formula (IV), are those of the formula

wherein W represents a lower aliphatic hydrocarbon radical of 1–4 C atoms and n=1–3, with the proviso, according to the above given definition of $R_3$, that the total number of C atoms be at least 9. In the case that n >1, the groups W are especially methyl.

The radical $R_1'$ can also be substituted by at most one free hydroxyl group or a hydroxyl group esterified with a monocarboxylic acid. As monocarboxylic acids there are especially to be mentioned those of the aliphatic series, especially lower aliphatic carboxylic acids with 1–7 C atoms, such as e.g. acetic or propionic acid, the butyric, valeric and caproic acids. Moreover, the esterified hydroxyl group can be derived from cycloaliphatic or cycloaliphatic-aliphatic carboxylic acids, such as e.g. the cyclopropane-, cyclobutane-, cyclopentane- or cyclohexane carboxylic acid, the cyclopropyl- or cyclobutylmethane carboxylic acids or the cyclopentyl- or cyclohexylethane carboxylic acid.

The said esterified hydroxyl group is, however, primarily derived from one of the long chain carboxylic acids mentioned below in connection with the group $R_2$.

The free or esterified hydroxyl group can also be present as a substituent in the radicals $R_1$ or $R_3$ containing ether groups, as specified above.

Among the compounds of formula (I) having one of the ester groups just mentioned there are to be singled out those in which $R_1$ has the formula

wherein $X_4$–$X_6$ each represent alkyl or alkenyl of 12–20 C atoms, $X_6$ being optionally also hydrogen, the alkyl or alkenyl groups being preferably one of the groups singled out above. There are of interest also corresponding compounds having a free hydroxyl group in place of the acyloxy group.

In the acyl group $R_2CO$ in the compounds of formula I and derivatives thereof, is a saturated or unsaturated, aliphatic or aliphatic-cycloaliphatic hydrocarbon radical which is also optionally substituted by oxygen functions and which has 11–21 C atoms, i.e. the acyl groups is derived from saturated or unsaturated, aliphatic or cycloaliphatic-aliphatic carboxylic acids which are optionally oxygenated in the hydrocarbon radical and which contain 12–22, preferably 14–18, C atoms. To be mentioned as such are the saturated or unsaturated fatty acids, such as lauric acid, myristic acid, palmitic acid, margaric acid, stearic acid, arachic acid, oleic acid, elaidic acid, linoleic acid, $\alpha$- and $\beta$-eleostearic acid, stearolic acid or $\alpha$-linolenic acid; and among the cycloaliphatic-aliphatic acids, e.g.: dihydrosterculic acid, malvalic acid, hydnocarpic acid and chaulmoogric acid. Oxygenated acids of this type, which are likewise suitable for the acyl group $R_2CO$, are, e.g., the acids obtained by epoxidation of the above-mentioned olefinic fatty acids and cycloaliphatic-aliphatic acids, e.g. $\gamma$,L-epoxystearic acid, also derivatives of the above-mentioned acids, which contain, e.g., one or more hydroxyl groups, such as ricinoleic acid.

An amino acid X or the amino acids of a sequence X according to formula (I) may be any D- or L-amino acids whose amino and carboxyl groups are each bonded to an aliphatic C atom, that is to say, one which is no part of an aromatic system. These amino acids are primarily "natural" amino acids, that is to say, those occurring in nature, as well as their antipodes and analogs.

The peptide sequence X in the compounds of formula (I) or their salts consists of a maximum of 10 amino acids, preferentially with at least half carrying a hydrophilic group, such as in particular hydroxyl, amino, carboxyl, carbamide, guanidino or imidazolyl groups. Of the ionic amino acids of this category there may be singled out among others those carrying acid groups, in particular aspartic acid and glutamic acid and oxyglutamic acid, and among those carrying basic groups especially lysine, ornithine, arginine and histidine. Amino acids having neutral character are in particular the amides, such as asparagine and glutamine, and those carrying hydroxyl groups are above all serine and threonine.

If X in the formula (I) represents the amino acid mentioned, it is likewise one of the specified amino acids, e.g. one carrying hydrophilic groups, e.g. especially serine or threonine.

Among the amino acids which can go into the above sequence and which carry no hydrophilic groups, there are to be mentioned in particular the unsubstituted amino acids, such as glycine, alanine, valine, norvaline, leucine, isoleucine and phenylalanine; also, however, some substituted amino acids which are of non-hydrophilic character, such as methionine, are of interest.

The sequence of the stated amino acids in the peptide chain X can be optional, but preferred sequences are those in which all the amino acids having hydrophilic groups are bound directly to each other, and among such are preferred those in which this sequence of hydrophilic amino acids is bound to the carboxyl group of the substituted cysteine or homo-cysteine part.

An important group of lipopeptides according to formula (I') encompasses compounds in which the peptide chain X consists of a maximum of 5 amino acids. Among such compounds the preferred ones are of the formula

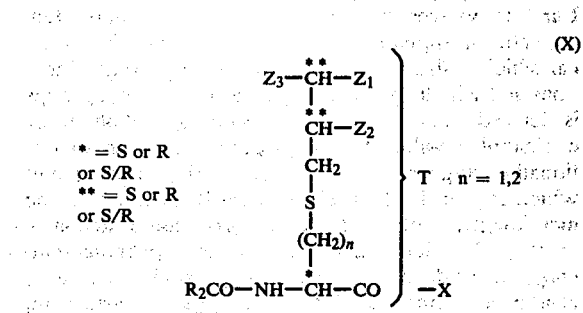

wherein $Z_1$, $Z_2$, $Z_3$ represent alkyl or alkenyl with 12-20 C atoms, or $Z_1$ and $Z_2$ the radicals $-C-Z_1'$ and $-O-Z_2'$, wherein $Z_1'$ and $Z_2'$ also represent alkyl or alkenyl with 12-20 C atoms, and $Z_3 = H$ or a radical $-CH_2-O-Z_3'$, wherein $Z_3'$ is alkyl or alkenyl with 12-20 C atoms, and X has the meaning as given for formula (I'), the number of amino acids being, however, limited to 2-5 in the case of X representing an aminoacids sequence, in which sequence preferentially at least the half of the amino acids carry hydrophilic groups, this also being the case when X represents one amino acid only, their salts and complexes. The following preferred lipopetide types of this group should be singled out:
(T is as defined for formula X)
T-Ser-Ser-Asn-Ala-Lys-OH
T-Ser-Ser-Asn-Ala-OH
T-Ser-Ser-Asn-OH
T-Ser-Ser-OH,
as well as the corresponding types, wherein serine is replaced by threonine, glutamine or asparagine, and compounds of the type
T-Ser-Ser-Asn-Ala-Glu-OH
T-Ser-Ser-Phe-Ala-Glu-OH
T-Ser-Ser-Phe-Ala-OH
T-Ser-Ser-Phe-OH
and corresponding types having threonine, glutamine or asparagine as replace amino acids for serine, and compounds of the type
T-Phe-Phe-Asn-Ala-Lys-OH
T-Glu-Gln-Asn-Ala-Lys-OH
T-Ser-Ser-Asn-Ala-Glu-OH
T-Ser-Ser-Asn-Ala-Ala-OH
T-Val-Lys-Val-Tyr-Pro-OH
T-Phe-Ile-Ile-Phe-Ala-OH
T-Ser-Ser-Phe-Ala-Glu-OH
T-Ser-Thr-Phe-Ala-Glu-OH
T-Ser-Phe-Ala-Glu-OH
T-Thr-Thr-Phe-Ala-Glue-OH
T-Ser-Ser-Asn-Ala-Lys-OH
T-Ser-Ser-Asn-Ala-D-Glu-OH
T-Ser-Ser-D-Asn-Ala-Glu-OH
T-Thr-Thr-Asn-Ala-Lys-OH
T-Ser-Thr-Asn-D-Ala-Lys-OH
T-Ser-Ser-Asn-Ala-Glu-OH
T-D-Ser-Ser-Phe-Ala-D-Glu-OH
and the amides and carboxylic acid esters with terminal carbamide or ester groups. Among these compounds the preferred ones are those in which the acyl radical $R_2-CO-$ is palmitoyl, stearoyl or oleolyl, $Z_3$ is hydrogen and $Z_1$ and $Z_2$ are identical alkoxy radicals and are preferably hexadecyloxy or octadecyloxy, further those in thich $Z_1$ and $Z_2$ are differend alkoxy radicals, preferably of the type just mentioned, and all these radicals may be present in any desired combination and/or variation. There may be mentioned as examples:

Compounds of formula X, wherein $R_2CO$=palmitoyl, $Z_1$ and $Z_2$=hexadecyloxy, $Z_3$=H, and X is one of the following sequences:
Ser-Ser-Asn-Ala-Lys-OH
Ser-Ser-Asn-Ala-OH
Ser-Ser-Asn-OH
Ser-Ser-OH
Ser-OH
or compounds according to formula IX, wherein $R_2CO$=stearoyl, $Z_1$ and $Z_2$=oxtadecyloxy, $Z_3$=H, or $R_2CO$=dihydrosterculoyl, $Z_1$ and $Z_2$=hexadecyloxy, $Z_3$=H, or $R_2CO$=lauroyl, $Z_1$ and $Z_2$=oxtadecenyloxy, $Z_3$=H, or $R_2CO$=lauroyl, $Z_1$ and $Z_2$=hexadecyloxy, $Z_3$=H, X being any of the sequences named above for the case of the N-palmitoyl derivative, moreover the compounds resulting from the substitution of serine by threonine, glutamic acid, glutamine, aspartic acid or asparagine and from the substitution of lysine by glutamic acid and of asparagine by phenylalanine.

All compounds mentioned relating to formula X may have the absolute R or S or S/R configuration at the *C atom as well as at either of the C atoms. The invention also encompasses in particular mixtures of diastereomers, which result from the variation of these possible configurations. There is to be particularly outlined the subgroup of compounds which have the R-configuration at the C atoms. A second group of lipopeptides according to the present invention comprises compounds of the formula X, in which X represents an amino acids sequence of 6-10 amino acids, the first 5 ot them having preferentially any of the sequences particularly named above. The amino acids 6-10 may be any of those specified above, especially serine, asparagine, alanine, glutamic acid, lysine, phenylalanine; they may occur for instance in the following sequences:
Ser-Ser-Asn-Ala-Lys-Ile-Asp-Glu-OH
-Ser-Ser-Asn-Ala-Lys-Asp-Glu-OH.

Specific compounds according to formula X having more than 5 amino acids in the sequence X are for instance those in which $R_2-CO$=dihydro-sterculoyl, $Z_1$ and $Z_2$=hexadecyloxy, $Z_3$=H, and X=Ser-Ser-Asn-Ala-Glu-Ile-Asp-Glu-OH, or $R_2-CO$=stearoyl, $Z_1$ and $Z_2$=hexadecyloxy, $Z_3$=H, and X=Ser-Ser-Asn-Ala-Glu-Ile-Asp-Glu-OH, or $R_2-CO$=palmitoyl, $Z_1$ and $Z_2$=hexadecyloxy, $Z_3$=H and X=Ser-Ser-Asn-Ala-Glu-Ile-Asp-Glu-OH, or $R_2$—CO=palmitoyl, $Z_1$ and $Z_2$=octadecyloxy, $Z_3$=H, and X=Ser-Ser-Asn-Ala-Lys-Ile-Asp-Glu-OH.

The specific definitions given for an amino acid X or for an amino sequence X in formula X are those also preferred for the compounds of formula (I'), and also for compounds having the formula, in which $R_1'$ has any of the partial formulae IV–V and VIII–IX.

In the above discussed new lipopeptides according to the present invention the terminal carboxyl group can be in the amide form. Besides the unsubstituted amide, there are applicable also those which are derived from a primary or secondary amine. Suitable in particular are amides of lower aliphatic amines having 1–7 C atoms, such as methylamine, ethylamine, propylamine, butylamine, dimethylamine, diethylamine or propyl- and isopropylamine, also aromatic amines, especially monocyclic amines, such as aniline or toluidine, araliphatic amines such as benzylamine, or heterocyclic amines, such as the aminopyridines. In the case of secondary aliphatic amines, these can be ring-closed nitrogen bases, such as pyrrolidine, piperidine or piperazine.

Specific amides are, e.g., the unsubstituted amides or the methyl-, ethyl-, dimethyl- or diethylamides of all the aformentioned specific lipopeptides according to the present invention, or amides of this type of the compounds described in the illustrative Examples.

In the esterified terminal carboxyl groups of the new lipopeptides, the alcohol constituent is derived preferably from lower aliphatic alcohols having 1–7 C atoms, such as methyl alcohol, ethyl alcohol, n-propyl alcohol, isopropyl alcohol or butyl alcohols. Th esterifying alcohols may however also be polyhydric alcohols, such as ethylene glycol or propylene glycol or glycerol. For esterification there can also be used araliphatic alcohols, particularly monocyclic lower aliphatic alcohols having 1–7 C atoms in the aliphatic part, such as benzyl alcohol, or heterocyclic alcohols, such as tetrahydrofuranol or tetrahydropyranol. As specific esters of this type of lipopeptides according to the invention there may be mentioned for example, the methyl and ethyl esters and the ethylene glycol or propylene glycol esters of all the aforementioned specific lipopeptides, or of those which are described in the illustrative Examples.

Depending on the nature of their substituents, the present new lipopeptides are neutral, acid or basic compounds. If excess acid groups are present, they form salts with bases, such as ammonium salts, or salts with alkali metals or alkaline-earth metals, e.g. sodium, potassium, calcium or magnesium; if however excess basic groups are present, they form acid addition salts.

Acid addition salts are in particular pharmaceutically applicable, nontoxic acid addition salts, such as those with inorganic acids, e.g. hydrochloric acid, hydrobromic acid, sulphuric acid or phosphoric acid, or with organic acids, such as organic carboxylic acids, e.g. acetic acid, propionic acid, glycolic acid, succinic acid, maleic acid, hydroxymaleic acid, methylmaleic acid, fumaric acid, malic acid, tartaric acid, citric acid, benzoic acid, cinnamic acid, mendelic acid, salicylic acid, 4-aminosalicylic acid, 2-phenoxybenzoic acid, 2-acetoxybenzoic acid, embonic acid, nicotinic acid or isonicotinic acid, or organic sulphonic acids, e.g. methanesulphonic acid, ethanesulphonic acid, 2-hydroxyethanesulphonic acid, ethane-1,2-disulphonic acid, benzenesulphonic acid, p-toluenesulphonic acid or naphthalene-1-sulphonic acid; and also other acid addition salts which can be used, e.g., as intermediates, e.g. for purification of the free compounds, or in the production of other salts, as well as for characterisation, for example those with picric acid, picroionic acid, flavianic acid, phosphotungstic acid, phosphomolybdic acid, chloroplatinic acid, Reinecke's acid or perchloric acid.

Complexes are the compounds formed with metal salts, e.g. with heavy-metal salts, such as salts of copper, zinc, iron or cobalt. To form such complexes, there are preferably used the phosphats, pyrophosphates and polyphosphates of these metal salts, optionally in combination with acid organic substances, e.g. polysaccharides containing acid groups such as carboxymethylcellulose, tannic acid, polyglutamic acid or partially hydrolysed gelatin, also alkali metal polyphosphates, such as "Calgon N", "Calgon 322", "Calgon 188" or "Plyron B 12".

The compounds of the present invention according to the above formula (I) and salts, complexes and mixtures thereof have valuable pharmacological properties, in particular they have a pronounced immunity-potentiating action. Thus the compounds in the dosage range of 0.5–320 µg/ml stimulate the proliferation of B-lymphocytes, which is determined in vitro by means of thymidine incorporation, 20-fold to 50-fold in comparison with control lymphocytes not stimulated. The extent of stimulation corresponds to that obtained with the most effective known B-cell mitogens [dextrane sulphate, E. coli Lipopolysaccharide, PPD (purified protein derivative)]; and in the case of the new compounds of the present invention even high concentrations do not have a lymphocytotoxic effect.

The new compounds of the formula (I) and the salts, complexes and mixtures thereof are moreover able, at a concentration of 0.3–60 µg/ml, to induce in splenocyte cultures of normal mice the formation of antibody-producing cells (propagation of the 195-plaque-forming cells by a factor of 20 to 50 with respect to the control value (in the absence of the stimulating substances)): In the presence of the stated compounds, there are thus formed, e.g., specific antibodies against sheep erythrocytes, without there being added to the cultures sheep erythrocytes for immunisation. On the other hand, the stated substances in the same concentration range are able to increase also the immunological reactivity of splenocyte cultures depleted of T-cells (of congenitally athymic nu/nu mice) compared with a normally thymus-dependent antigen (sheep erythrocytes) [factor 10 to 40 compared with untreated control cultures]. The action of the stated compounds is however not only to induce in vitro, directly or indirectly, proliferation and synthesis performance of B-lymphocytes (i.e. of potentially antibody-forming cells), but also to induce effects on T-lymphocytes (to which belong supporting cells, suppressor cells and also cytotoxic effector cells which are active as regulators). Thus, for example, towards allogenic irratiated stimulator lymphocytes, the said compounds in a concentration range of 10–100 µg/ml are capable of substantially potentiating the reactivity of cortisone-resistant thymus cells (up to 10-fold).

The effects mentioned above are probably indirectly a result of the lipopetides activating macrophages which, in their turn, promote the reactivity of T- and B-lymphocytes. It can in fact be shown that the stated compounds, even at an extremely low concentration (0.01–10 µg/ml), release large amounts of "colony stimulating activity" (CSA) from mouse macrophages (induction of up to 150–200 colonies within 7 days from $10^5$ mouse marrow cells, after addition of 20% of the supernatants from macrophage cultures incubated during 24 hours with substance, in comparison with 0–5 colonies with the addition of supernatants from untreated macrophage cultures). CSA is a biological mediator which is necessary for differentiation of bone-marrow parent cells with respect to macrophages and polymorphonuclear leucocytes. The stated compounds hence effect an increased supply of cells which are of extreme importance for the non-specific resistance and for the induction amplification and expression of specific (lymphocyte-induced) immune reactions.

The immunity-potentiating action of the new compounds of the formula (I) and of salts, complexes or mixtures thereof can be verified also in vivo. Thus the injection of a lipopeptide according to the invention leads within 3–9 hours to a high increase of the CSA concentration in the serum (up to 120 colonies per $10^5$ mouse narrow cells after the addition of serum extracted with chloroform [5% final concentraton], compared with 0–5 colonies in the case of untreated animals). Accordingly, the antibody-forming capacity of mice is greatly potentiated by administration of the same compounds in vivo.

NMRI mice are immunised by intraperitoneal injection of 10 μg of precipitate-free BSA on day 0. Serum samples are taken 9, 15 and 29 days later and tests are carried out, using a passive haemagglutination technique, to determine their content of anti-BSA antibodies. In the employed dosage amount, soluble BSA is subimmunogenic for the receiver animals, that is to say it is not able to initiate any production of antibodies or is able to initiate only a very slight production of antibodies. Additional treatment of the mice with specific immunity-potentiating substances before or after administration of the antigen leads to a rise in the antibody titre in the serum. The effect of the treatment is expressed by the score value attained, that is to say by the sum of the $\log_2$ titre differences on the three days when blood is sampled. In this test, the compounds of the formula (I) and salts, complexes or mixtures thereof are able, on intraperitoneal or subcutaneous administration of 0.03–3 mg/kg of animal weight on five consecutive days, before or after immunisation with BSA to significantly increase the production of antibodies against BSA.

Also manifestations of the cell-transmitted immunity can be potentiated by the said compounds in vivo.

Whereas sensibilisation of guinea pigs with BSA in incomplete Freund's adjuvant leads only to humoral antibody formation, the addition of the lipopeptides according to the present invention in a dosage range of 1–15 μg, to the aqueous phase of the antigen-oil emulsion induces delayed-type hypersensitivity towards BSA. Three weeks after immunisation, the intracutaneous injection of BSA in the case of these animals leads to a local inflammatory reaction with erythema and thickening of the skin, which attains its maximum within 24 to 48 hours. These delayed-type reactions correspond quantitatively and qualitatively to those which are usually obtained by immunisation with BSA in complete Freund's adjuvant (i.e. with addition of mycobacteria). The $ED_{50}$ values (required μg/animal for the induction of a difference in the reaction volume (surface area of the erythema × increase in thickness of skin) in the case of treated and untreated animals of 200 μl, 24 hours after induction) are 2–3 μg.

The lipopeptides according to the present invention are moreover nigligibly toxic. Even intraperitoneal administration five times in a dosage amount of 10 mg/kg/day on five consecutive days was tolerated by the mice without there being any apparent symptoms. Since the doses necessary for immunity-stimulation are very low, the therapeutic range of the new compounds is extremely wide.

The new lipopeptides according to the present invention can therefore substantially increase the cellular and, in particular, the humoral immunity, both when administered in admixture with the antigen itself (adjuvant effect in the narrower sense) and when supplied at times and places which differ from those of the antigen injection (systemic immunity potentiation).

The new lipopeptides according to the present invention can hence be used as adjuvants in admixture with vaccines to improve the success rate of the vaccination, and to improve the protection imparted by humoral antibodies and or cellular immunity against infection by bacterial, viral or parasitic pathogens.

Finally, the compounds described are suitable, in admixture with various antigens, as adjuvants for the experimental and industrial manufacture of antisera for therapy and diagnosis, and for inducing immunologically activated lymphocyte populations for cell-transfer processes.

Furthermore, the new lipopeptides can be used, even without the stimultaneous administration of an antigen to promote immune reactions which are already taking place subliminally in humans and animals. Accordingly, the compounds are especially suitable for stimulating the body's own resistance, e.g. in the case of chronic and acute infections, or in the case of selective (antigen-specific) immunological defects; and also in the case of general (that is to say not antigen-specific) immunological defective states which are congenital or acquired, such as arise in old age, in the course of severe primary diseases and, above all, after therapy with ionising rays or with hormones having an immuno-suppressive action. The said substances can thus be administered, preferably also in combination with antibiotics, chemotherapeutic agents or in combination with other therapeutical treatments, in order to counteract immunological damage. Finally, the substances described are suitable also for the general prophylaxis of infectious diseases in humans and in animals.

The new lipopeptides can be produced by methods known per se, or by new processes which are described herein.

The compounds of the formula (I) and diastereoisomeric mixtures, salts and complexes thereof are produced by a preferred process which is characterised in that

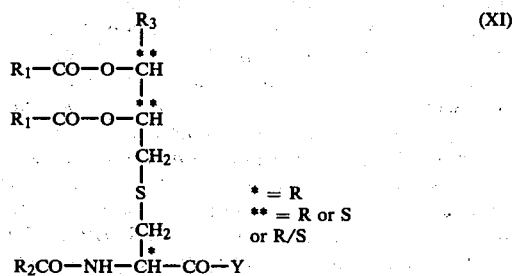

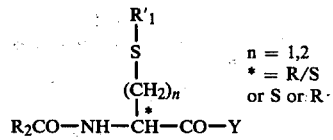
(XII)

wherein $R_1$, $R_2$ and $R_1'$ have the meanings given under the formula (I) and (I') and Y represents an amino acid or amino acid sequence corresponding to X in the formula (I) or (I'), wherein however at least one of the to X in the formula (I) or (I'), wherein however at least one of the hydrophilic groups substituting the amino acids and/or the terminal carboxyl group is (are) protected by a protective group which can be split off under neutral or mild acid conditions, or in a salt of such a compound, the protective group(s) is (or are) split off; or (b) a compound of the formula

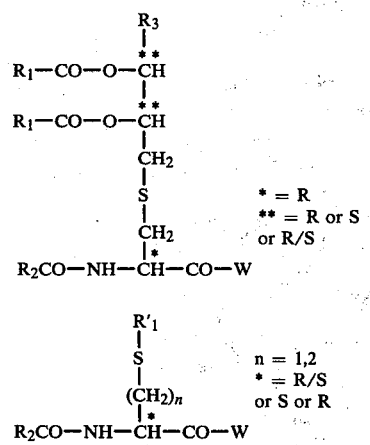
(XIII)

(XIV)

wherein $R_1$, $R_2$ and $R_1'$ have the meanings given under the formula (I) and (I'), and W represents OH or an amino acid or an incomplete sequence of amino acids with respect to N in the formulae (I) and (I') is reacted with a compound of the formula $NH_2 - Z_1$ (XV)

wherein $Z_1$ represents a group corresponding to the group X in the formula (I) or (I') or an amino acid sequence or an amino acid complementary to the stated amino acid or incomplete sequence of amino acids in W with respect to X, in which sequence however no free amino groups are present, or with a salt thereof; or (c) in a compound according to formula (I'), in which in the radical $R_1'$ at least one free hydroxyl group is present, but no free hydroxyl groups are present in X, the free hydroxyl groups are etherified or (d) in a compound according to formula (I'), in which in the radical $R_1'$ there is present a free hydroxyl group, but no free hydroxyl groups are present in the radical X, the free hydroxyl group is esterified by treatment with an acylating agent or (e) a compound of the formula

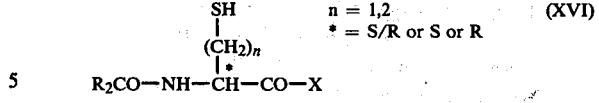
(XVI)

wherein $R_2$ and X have the same meaning as in formula (I'), but no free hydroxyl groups are present in X, is treated with an acylating agent, or (f) a compound of the formula

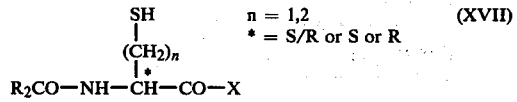
(XVII)

wherein $R_2$ and X have the same meaning as in formula (I'), is treated with a compound of the formula $R_1 - T$ (XVIII)

wherein T represents a reactive functionally modified hydroxyl group in the presence of a basic medium, or (g) a compound of the formula

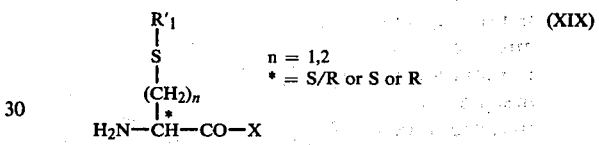
(XIX)

wherein X and $R_1'$ have the same meaning as given for formula (I) but no hydroxyl and amino groups are present in X, is treated with an acylating agent or, (h) a compound of the formula

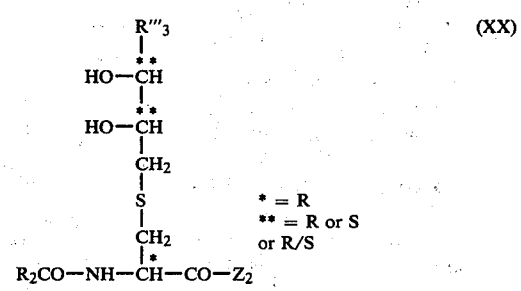
(XX)

wherein $R_2$ has the meaning given under formula (I), and $R'''$ represents hydrogen or the group $HO-CH_2-$, and $Z_2$ represents a group corresponding to X in the formula (I), wherein, however, no free hydroxyl groups are present, or a salt of this compound, is acylated in a manner known per se, and, if required, in resulting compounds having a free terminal carboxyl group this group is converted into an amide group or ester group, and/or the compounds are converted into salts or complexes thereof.

The protective groups in the process according to variante (a) are, in particular, those known from the synthesis of peptides.

Thus, for example, protective groups for amino groups are acyl or aralkyl groups such as formyl, trifluoroacetyl, phthaloyl, benzenesulphonyl, p-toluenesulphonyl, o-nitrophenylsulphenyl and 2,4-dinitrophenylsulphenyl groups (these sulphenyl groups can also be split off by reaction with nucleophilic reagents, e.g.

sulphites or thiosulphates); benzyl, or diphenyl- or triphenylmethyl groups which are optionally substituted, e.g. by lower alkoxy groups, especially by o- or p-methoxy groups; or groups derived from carbonic acid, such as arylmethyloxycarbonyl groups optionally substituted in the aromatic rings, e.g. by halogen atoms such as chlorine or bromine, nitro groups, lower alkyl or lower alkoxy groups or by chromophoric groups, e.g. azo groups, in which the methylene group can be substituted by a further aryl group and/or by one or optionally two alkyl groups, such as benzyl-, benzhydryl- or 2-phenyl-isopropyloxycarbonyl groups, e.g. carbobenzoxy, p-bromo- or p-chlorocarbobenzoxy, p-nitrocarbobenzoxy or p-methoxycarbobenzoxy, p-phenylazo-benzyloxycarbonyl and p-(p'-methoxy-phenylazo)-benzyloxycarbonyl, 2-tolyl-isopropyloxycarbonyl and, in particular, 2-(p-biphenylyl)-isopropyloxycarbonyl, as well as aliphatic oxycarbonyl groups such as adamantyloxycarbonyl, cyclopentyloxycarbonyl, trichloroethyloxycarbonyl, tert-amyloxycarbonyl or, in particular, tert-butyloxycarbonyl.

The amino groups can also be protected by the formation of enamines, obtained by reaction of the amino group with 1,3-diketones, e.g. benzoylacetone, acetylacetone or dimedone.

Carboxyl groups are protected for example by amide or hydrazide formation or by esterification. The amide and hydrazide groups can be optionally substituted: the amide group e.g. by the 3,4-dimethoxybenzyl or bis-(p-methoxyphenyl)-methyl group; the hydrazide group e.g. by the carbobenzoxy group, the trichloroethyloxycarbonyl group, the trifluoroacetyl group, the trityl group, the tert-butyloxycarbonyl group or the 2-(p-biphenylyl)-isopropyloxycarbonyl group. Suitable for esterification are, e.g., lower optionally substituted alkanols such as methanol, ethanol, cyanomethyl alcohol, benzoylmethyl alcohol or, in particular, tert-butanol, also aralkanols such as aryl-lower-alkanols, e.g. benzyl alcohols, p-nitrobenzyl alcohol, p-methoxybenzyl alcohol, 2,4,6-trimethylbenzyl alcohol, or benzhydrols such as benzhydrol, all optionally substituted by lower alkyl or lower alkoxy groups or halogen atoms; phenols and thiophenols optionally substituted by electron-attracting substituents, such as thiophenol, thiocresol, p-nitrothiophenol, 2,4,5- and 2,4,6-trichlorophenol, pentachlorophenol, p-nitrophenol, 2,4-dinitrophenol, p-cyanophenol or p-methanesulphonylphenol; also e.g. N-hydroxysuccinimide, N-hydroxyphthalimide, N-hydroxypiperidine and 8-hydroxyquinoline.

The hydroxyl groups of the serine and threonine groups can be protected for example by esterification or etherification.

Suitable acyl groups in the case of esterification are in particular radicals derived from carbonic acid, such as benzoyloxycarbonyl or ethyloxycarbonyl. Groups suitable for etherification are, e.g., benzyl, tetrahydropyranyl or tert-butyl groups. Suitable for protecting the hydroxyl groups are also the 2,2,2-trifluoro-1-tert-butyloxycarbonylamino or -1-benzyloxycarbonylaminoethyl groups (Weygand) described in Ber. 100 (1967), 3338–3849.

Preferably, the tert-butyl ester group or the benznydrol group is used for protecting the carboxyl group of the side chains and optionally the terminal carboxyl group; the tert-butyloxycarbonyl group for protecting the amino groups of the side chains; the tert-butyl ether group for protecting the hydroxyl groups or serine or threonine; and, optionally, the 2,2,2-trifluoro-1-tert-butyloxycarbonylaminoethyl group for protecting the imino group or histidine.

The splitting-off of the protective groups according to the process with acid agents under mild conditions can be effected in a manner known from peptide chemistry, e.g. by treatment with trifluoroacetic acid.

A particular protective group for carboxyl groups, which group can be split off under neutral conditions, is the group described e.g. in the German Offenlegungsschrift No. 27 06 490, this group being of the general formula

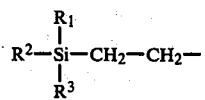

wherein $R^1$, $R^2$ and $R^3$ each represent a hydrocarbon radical, whereby the radicals may also be linked with each other by a simple C—C bond, in particular alkyl groups having 1–5 C atoms. Protective groups of this type are, e.g., the 2-(dimethyl-tert.-butylsilyl)-ethyl group, the 2-(dibutyl-methylsilyl)-ethyl group and particularly the 2-(trimethylsilyl)-ethyl group. Although these protective groups can also be split off basically, it is in particular the splitting-off of these groups under neutral conditions which is of interest, for instance by reaction with a salt of hydrofluoric acid. The protective group is advantageously split off in an aprotic organic solvent; it is preferable in this respect to avoid the presence of those solvents which are able to solvate the fluoride anion, such as water or lower aliphatic alcohols.

The condensation according to the variant (b) of the compounds of the formulae (XIII) or (XIV) with the compounds of the formula (XV) is performed, for example, by reacting the compounds (XIII) or (XIV) in the form of the activated carboxylic acid with (XV); or by reacting the acids (XIII) or (XIV) with the compound (XV) of which the amino group is in the activated form. The compounds (XIII)–(XV) are used optionally in the form of their salts for the condensation reaction.

The carboxyl group of the compounds (XIII) or (XIV) can be activated for example by conversion into an acid azide, acid anhydride, acid imidazolide or acid isoxazolide, or into an activated ester, such as cyanomethyl ester, carboxymethyl ester, thiophenyl ester, p-nitrothiophenyl ester, thiocresyl ester, p-methanesulphonylphenyl ester, p-nitrophenyl ester, 2,4-dinitrophenyl ester, 2,4,5- or 2,4,6-trichlorophenyl ester, pentachlorophenyl ester, N-hydroxysuccinimide ester, N-hydroxyphthalimide ester, 8-hydroxyquinoline ester, 2-hydroxy-1,2-dihydro-1-carbethoxy-quinoline ester, N-hydroxypiperidine ester or an enol ester, which is obtained with N-ethyl-5-phenyl-isoxazolium-3-sulphonate [Woodward reagent]; or by reaction by means of a carbodiimide (optionally with the addition of N-hydroxysuccinimide), or by means of a 1-hydroxybenzotriazole, 3-hydroxy-4-oxo-3,4-dihydrobenzo[d]-1,2,3-triazine or N,N'-carbonyldiimidazole, each of which is unsubstituted or substituted, e.g., by halogen, methyl or methoxy.

The amino group of the compound (XV) can be activated for example by reaction with a phosphite.

The most customary methods of condensation to be mentioned are: the method according to Weygand-Wünsch (carbodiimide in the presence of N-hydroxysuccinimide), the azide method, the N-carboxyanhydride or N-thiocarboxyanhydride method, the activated ester method and the anhydride method. These condensation reactions can be performed in particular by the Merrifield method.

It is also possible to perform the condensation of the compounds XIII and XIV, using the above-mentioned methods, with a compound corresponding to the formula (XV) in which the terminal carboxyl group is blocked by a protective group which is different from an amide or ester group as defined for X, such as by one of the aforementioned groups, and/or one or more of the hydrophilic groups present is in the protected form, as described above. There are thus obtained condensation products which belong to the group of starting materials of the formula (XI) to (XII) used for the variant (a) described in the foregoing, and which are likewise subject matter of the present invention.

According to the above variants (c), (d), (e) and (h) free hydroxyl groups are etherified or acylated respectively in compounds of formulae (I), or (I'), which have not to contain free hydroxyl groups in the X part, in $R_1'$ or the SH-group in compounds of formula (XVI).

The acylation can be performed in a manner known per se, e.g. by reaction with a reactive functional derivative of the acid corresponding to the radical to be introduced, such as with the anhydride or an acid halide, preferably in the presence of a tertiary base, such as pyridine or collidine. Free amino groups in the X moiety would also be esterified, and hence they have to be protected, e.g. by conversion into a salt, e.g. the hydrochloride before carrying out the acylation.

This process is particularly suitable for producing products according to the formula I in which the acyl groups in the radical $R_1$ are different from the acyl group $R_2$.

The etherification of free hydroxyl groups according to the above process (c) can also be effected in a manner known per se, e.g. by treatment with an alkyl or alkenyl halide in the presence of a base, e.g. silver oxide, or especially with a diazoalkane, such as a lower aliphatic diazoalkane with 1-3 C atoms, primarily with diazomethane, for instance in an ethereal solution. This method is especially suitable for the manufacture of compounds with a radical $R_1'$ according to partial formula (VIII).

If these etherifications or acylations are performed in the case of compounds according to formula (I) having free hydroxyl groups in $R_1'$ and which, however, in the part X the terminal carboxyl group is protected by protective groups other than an amide or ester group as defined for X, and/or in which one or more of the hydrophilic groups present is in the protected form as described above, there are likewise obtained starting compounds for the above variant (a).

In the lipopeptides according to the formula I which are obtained by any of the process variants described and in which there is a free terminal carboxyl group in the X part, this group can be converted in a manner known per se, e.g. by one of the methods customary in peptide chemistry, into the amide or ester group.

A compound of formula (XVI) above in which W=OH, to be used as starting material, may be obtained by condensation of the substituted cystein or homocystein of the formula $$R_2CO-NH-\underset{\underset{\underset{*}{|}}{\underset{(CH_2)_n}{|}}}{\overset{SH}{\underset{|}{C}H}}-CO-OH \quad \begin{array}{l} n = 1,2 \\ * = S/R \text{ or } S \text{ or } R \end{array} \quad (XXI)$$

wherein $R_2$ has the same meaning as in formula (I'), in the presence of a basic medium with a compound of the formula $$R_1-T \qquad (XXII)$$

where T is a reactive, functionally modified hydroxyl group. For carrying out this condensation the cysteine or homocysteine carboxyl group is protected intermediately with any protective group known in peptide chemistry.

The condensation reaction according to method (f) above is also performed in a manner known per se. A reactive functionally modified hydroxyl group T is for example an esterified hydroxyl group, especially a hydroxyl group esterified with an aliphatic or aromatic-aliphatic sulfonic acid, e.g. a lower aliphatic sulfonic acid with 1-7 C atoms or a monocyclic aromatic sulfonic acid, such as a benzene sulfonic acid. There are used primarily p-toluene sulfonic acid esters as compounds of the formula XVIII.

A reactive esterified hydroxyl group is also a halogen atom, for instance chlorine, bromine or iodine, or especially also an epoxide group.

A basic medium suitable for carrying out the condensation is a weakly basic or strongly basic compound, such as an alkali metal or alkaline earth metal hydride or magnesium hydride, an alkali salt of a weak acid, such as sodium or potassium carbonate. If halogen compounds are used for the condensation, silver oxide is also a preferred basic medium to be used. When an epoxide is used for conversation there is also preferably used an alkali metal salt of a weak acid as condensing agent, especially sodium or potassium carbonate.

In the acylation method according to the variant (g) above the starting compound of formula XIX is treated with an acylating agent capable of introducing the acyl radical $R_2CO-$, $R_2$ having the same meaning as in formula I'. The conditions under which this acylation is conducted are the same as described above for the variants (d), (e) or (h). In particular care should be taken that free amino groups in the peptide chain X be converted into its salt form, e.g. into a hydrochloride or a quaternary ammonium salt.

The amino acids and peptides to be used for producing by the processes of the invention the new lipopeptides are known, or they can be produced by methods known per se.

All starting compounds for the above described processes (a) to (h) are known or can be prepared in a manner known besides those already described per se. For instance a compound according to formula XIX may be prepared from a corresponding compound in which the amino group is in protected form, the protecting group being one of those known e.g. in peptide synthesis, and such starting materials, in turn, can be obtained from the corresponding protected cysteine by reaction with a compound $R_1'-T$ as described above.

Compounds of formula XIII or XIV in which W represents an amino acid or sequence of amino acids complementary to the full sequence X to be used as starting materials according to variant (b) above can be obtained by methods analogous to the above variants (a) or (b).

The above starting compounds XIII and XIV for the variant (b) in the case where W=OH, and also diastereoisomeric mixtures, salts and complexes thereof, themselves have also an immunity-potentiating action, and this action occurs in vitro in the same dosage range as that in which it occurs on application of the compounds of the formula I and derivatives thereof. The stated compounds produce in vivo in the above-described test for potentiation of the humoral immunity, with intraperitoneal administration 5 days before administration of the antigen, an increase of the antibody titres in the serum in the dosage range of 1.0 to 3 mg/kg of animal weight.

Compounds of formulae XIV can be obtained for instance by protecting the amino and optionally also the carboxyl group in a compound of the formula

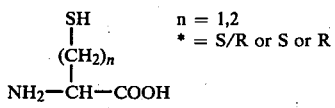

and reacting the compound so obtained with a compound $$R_1'—T$$

$R_1'$ having the same meaning as in formula (I) and T representing a reactive functionally modified hydroxyl group, in a basic medium, according to the methods described above for similar processes. After the condensation the protecting groups are, if desired, removed in a manner known per se.

Compounds of the formula XIII can be obtained by acylation of a compound according to formula XX in which, however, a hydroxyl group is present in place of $Z_2$, as described above for variant (h). The starting material required, i.e. the glyceryl- and erithrityl-N-acyl-cysteines, can be prepared as follows:

An N-acyl- or N,O,O-triacyl-S-(2,3-dihydroxypropyl)-cysteine according to the formula (VII), which is to be used as starting material, can, if W=OH and $R_3$=H, be obtained in the following manner: starting with 1.1, 5.6-D-mannitol diacetonide, there is obtained, by periodate oxidation, 2-O,3-O-isopropylidene-D-glycerol aldehyde; the aldehyde group is then reduced to the carbinol group, and this is esterified with p-toluenesulphonic acid. The 1-O-tosyl-2(R)-O,3-O-isopropylidene glycerol thus obtained is condensed with N-acyl-(S)-cysteine in the presence of a basic agent, e.g. potassium carbonate, and there is thus obtained N-acyl-S-[2(R),3-isopropylenedioxy-propyl]-(S)-cysteine, which is saponified by an acid reaction, e.g. with acetic acid. The resulting N-acyl-S-[2(R),3-dihydroxypropyl]-(S)-cysteine can, if required, be further acylated in the 2- and 3-positions of the glycerol moiety, preferably with temporary protection of the carboxyl group, e.g. by means of the above-described trimethylsilylethyl group, or preferably the benzhydryl ester group.

To produce an N-acyl- or N,O,O,O-tetraacyl-S-(2,3,4-trihydroxybutyl)-cysteine to be used as starting material according to the formula (VII), the method employed can be analogous to the method of Example 7.

Compounds of the formula XX in which $Z_2$ has a meaning corresponding to that of group X in the formula (I), and in which, however, no free hydroxyl groups are present, can be obtained by reaction of the N-acyl-cysteine derivatives just mentioned with a compound of the formula $NH_2—Z_2$ according to the same principles as for the above described variant (b) of the general process for the production of the lipopeptides according to the invention.

The lipopeptides obtained can be converted into their salts in a manner known per se, e.g. by reaction of resulting acid compounds with alkali metal hydroxides or alkaline-earth metal hydroxides, or of resulting basic compounds with acids.

By virtue of the close relationship between the new compounds in the free form and in the form of salts and complexes thereof, it is to be unterstood, in the foregoing and in the following, that by the term "free compounds" is meant, where the case applies and with the appropriate modifications, also the corresponding salts.

By virtue of the physical-chemical differences in their constituents, isomeric mixtures obtained can be separated in a known manner, for example by chromatography and/or by fractional crystallisation. Advantageously, the more active of the isomers is isolated.

The processes described above are performed e.g. by methods known per se, in the absence or preferably in the presence of diluting agents or solvents, if necessary with cooling or heating, under elevated pressure and/or in an inert gas, such as in a nitrogen atmosphere. With due regard being given to all substituents present in the molecule, there are to be used if necessary, especially where readily hydrolysable O-acyl groups are present, particularly gentle reaction conditions, such as short reaction times, use of mild acid agents at low concentration, stoichiometric quantity ratios, and choice of suitable catalysts, solvents, temperature and/or pressure conditions.

The invention relates also to those modifications of the process whereby a compound occurring as an intermediate at some stage of the process is used as the starting material and the uncompleted steps are performed; or whereby the process is interrupted at any stage; or whereby a starting material is formed under the reaction conditions, or is used in the form of a reactive derivative or salt. There are preferably used those starting materials by which are obtained, according to the process of the present invention, the compounds which have been described in the foregoing as being particularly valuable.

The present invention relates likewise to pharmaceutical preparations which contain the described new lipopeptides according to the invention, both of the formula (I) and those of the formula (XI), and to mixtures, salts or complexes thereof. The pharmaceutical preparations according to the invention are preparations which are for enteral administration, such as oral or rectal as well as parenteral administration, to warm-blooded animals, and which contain the pharmacological active substance on its own or together with a pharmaceutically applicable carrier material. The dosage of active substance depends on the species, on the age and on the individual condition of the warm-blooded animal concerned, and also on the mode of administration. Thus, for instance, daily doses in the range between 1-30 mg/kg body weight of the new lipopeptides by sub-cutaneous administration and in the range between 0,3-3 mg/kg body weight on intraperitoneal administration are administered to obtain an immunopentiating effect.

The new pharmaceutical preparations contain from about 10% to about 95%, preferably from about 20% to about 90%, of active substance. Pharmaceutical preparations according to the invention can be, e.g., in the form of dosage units, such as dragees, tablets, capsules, suppositories or ampoules.

The pharmaceutical preparations of the present invention are produced in a manner known per se, e.g. by means of conventional mixing, granulating, coating, solution or lyophilising processes.

Suitable carrier substances are in particular fillers, such as sugar, e.g. lactose, saccharose, mannitol or sorbitol, cellulose preparations and/or calcium phosphates, e.g. tricalcium phosphate or calcium hydrogen phosphate; also binders such as starch mucilage, with the use e.g. of maize starch, wheat starch, rice starch or potato starch, gelatine, tragacanth, methylcellulose, hydroxypropylmethylcellulose, sodium carboxymethylcellulose and/or polyvinylpyrrolidone, and/or, if desired, effervescent agents, such as the afore-mentioned starches, also carboxymethyl starch, cross-linked Polyvinylpyrrolidone, agar, alginic acid or a salt thereof, such as sodium alginate. Auxiliaries are in particular flow-regulating agents and lubricants, e.g. silicic acid, talcum, stearic acid or salts thereof, such as magnesium stearate or calcium stearate, and/or polyethylene glycol. Dragée cores are provided with suitable coatings, optionally resistant to gastric juices; for this purpose there are used, inter alia, concentrated sugar solutions which optionally contain gum arabic, talcum, polyvinylpyrrolidone, polyethylene glycol and/or titanium oxide, lacquer solutions in suitable organic colvents or solvent mixtures, or, for producing coating resistant to gastric juices, solutions of suitable cellulose preparations, such as acetylcellulose phthalate or hydroxypropylmethylcellulose phthalate. Dyes or pigments may be added to the tablets or dragée coatings, e.g. for identification or for indication of the various doses of active substance.

The following Examples illustrate the invention described in the foregoing; they are however not intended in any way to limit the scope of this invention. Temperatures are given in degrees Centigrade.

The abbreviations used are as follows:
Z=carbobenzoxy
$Bu^t$=tert-butyl ester
O $Bu^t$=tert-butyl ester
BOC=tert-butoxycarbonyl
DMF=dimethylformamide
ONp=p-nitrophenyl ester
HOBt=N-hydroxybenzotriazole
DC=thin-layer chromatography
Me=$CH_3$
OTmse=trimethylsilyl-ethyl-group
Sn=Succinimido In DC there is used silica gel as adsorbent, and the following systems are used as eluants:
system 3: ethyl acetate/pyridine/water (65:20:15),
system 157: chloroform/methanol/water/glacial acetic acid (70:42:10:0.5),
system 157c: chloroform/methanol/water/glacial acetic acid (75:25:5:0.5),
system 157A: chloroform/methanol/water/glacial acetic acid (90:10:1:0.5).

EXAMPLE 1

1.13 g of N-palmitoyl-S-[2(R),3-dipalmitoyloxypropyl]-Cys-Ser-($Bu^t$)-Ser($Bu^t$)-Asn-OBut is taken up in 5 ml of 90% trifluoroacetic acid, and after 45 minutes at 20° the solution is concentrated by evaporation to about 2 ml. The product is precipitated by the addition of 75 ml of peroxide-free ether, filtered off, and dried over potassium hydroxide. The lipopeptide N-palmitoyl-S-[2(R),3-dipalmitoyloxypropyl]-Cys-Ser-Ser-Asn-OH thus obtained gives in the thin-layer chromatogram on silica gel the following Rf values: Rf (chloroform/methanol/glacial acetic acid/water 79:25:0.5:4.5)=0.25.

0.89 g of N-palmitoyl-S-[2(R),3-dihydroxypropyl]-Cys-Ser ($Bu^t$)-Ser($Bu^t$)-Asn-OBu$^t$ is taken up in 10 ml of pyridine; 0.725 ml of palmitic acid chloride is added, and the solution is kept at 45° for 24 hours. There is then added 200 ml of chloroform, and the solution is extracted with 1 N citric acid, 1 N sodium bicarbonate and water; the organic phase is dried over sodium sulphate, and the solvent is evaporated off. The residue is purified by chromatography on silica gel in the system chloroform, or chloroform/methanol (98:2). The thin-layer-chromatographically homogeneous lipopeptide-N-palmitoyl-S-[2(R),3-dipalmitoyloxypropyl]-Cys-Ser-($Bu^t$)-Ser($Bu^t$)-Asn-OBu$^t$ gives in the system chloroform/methanol (9:1) on silica gel an Rf value of 0.75.

To 0.90 g of N-palmitoyl-S-[2(R),3-dihydroxypropyl-(L)-cysteine and 0.99 g of H-Ser($Bu^t$)-Ser($Bu^t$)-Asn-OBu$^t$ in 20 ml of dimethylformamide are added at 0° 0.472 g of dicyclohexylcarbodiimide and 0.309 g of N-hydroxybenzotriazole. After 2 hours at 0° and 15 hours at 20°, the product is filtered off and the filtrate is concentrated by evaporation. The residue is purified by chromatography on a column of silica gel in the system chloroform/methanol (98:2). In the thin-layer chromatogram on silica gel, the resulting lipopeptide derivative N-palmitoyl-S-[2(R),3-dihydroxypropyl]-Cys-Ser-$Bu^t$)-Ser ($Bu^t$)-Asn-OBu$^t$ gives an Rf value of 0.60 (chloroform/methanol 8:2).

6.09 g of Z-Ser($Bu^t$)-Ser($Bu^t$)-Asn-OBu$^t$ is dissolved in 60 ml of methanol and the solution, after the addition of 0.5 g of Pd-charcoal (10%), is hydrogenated at room temperature for 3 hours. The catalyst is filtered off, and the filtrate is concentrated by evaporation. The product is obtained as white foam. In the thin-layer chromatogram on silica gel, the resulting peptide H-Ser($Bu^t$)-Ser($Bu^t$)-Asn-OBu$^t$ gives an Rf value of 0.41 in the system chloroform/methanol (8:2).

4.134 g of Z-Ser($Bu^t$)-OH and 4.64 g of H-Ser($Bu^t$)-Asn-OBu$^t$ are dissolved in 50 ml of dimethylformamide, and at 0° there are added 3.172 g of dicyclohexylcarbodiimide and 1.89 g of N-hydroxybenzotriazole. After 2 hours at 0° and 15 hours at 20°, the dicyclohexylurea which has precipitated is filtered off with suction, the filtrate is concentrated by evaporation, the residue is taken up in ethyl acetate, and the solution is extracted with 1 N citric acid, 1 N sodium bicarbonate and water, dried over sodium sulphate and then concentrated by evaporation. The residue is recrystallised from ethyl acetate/hexane to yield peptide Z-Ser($Bu^t$)-Ser($Bu^t$)-Asn-OBu$^t$ having a melting point of 96°-98°; on silica gel: Rf (chloroform/methanol 95:5)=0.25.

4.65 g of Z-Ser($Bu^t$)-Asn-OBu$^t$ in 50 ml of methanol is hydrogenated in the presence of 0.4 g of Pd-charcoal (10%). The catalyst is filtered off and the filtrate is concentrated by evaporation to yield peptide H-Ser(-$Bu^t$)Asn-OBu$^t$ in the form of white foam; on silica gel: Rf (chloroform/methanol 7:3)=0.48.

5.9 g of Z-Ser($Bu^t$)-OH and 3.76 g of H-Asn-OBu$^t$ are dissolved in 60 ml of dimethylformamide, and at 0° there are added 3.06 g of N-hydroxybenzotriazole and 4.53 g of dicyclohexylcarbodiimide. After 2 hours at 0° and 15 hours at 20°, the resulting product is filtered off, the filtrate is concentrated by evaporation, and the residue is crystallised from ethyl acetate/petroleum ether. The peptide Z-Ser(Bu$^t$)-Asn-OBu$^t$ obtained melts at 114°–115°. $[\alpha]_D^{20} = +4°$ (c=1.5 in methanol); on silica gel: Rf (chloroform/methanol 9:1)=0.48.

EXAMPLE 2

1.6 g of N-palmitoyl-S-[2(R),3-dipalmitoyloxypropyl]-Cys-Ser(Bu$^t$)-Ser(Bu$^t$)-Asn-Ala-OBu$^t$ is dissolved in 7.5 ml of 90% trifluoroacetic acid, and after 15 minutes at 20° the solution is concentrated by evaporation to about 2 ml. The product is precipitated with 100 ml of ether; it is then filtered off and subsequently dried over sodium hydroxide to yield, in the form of a white powder having a melting point of 215°–217° (decomposition), lipopeptide N-palmitoyl-S-[2(R),3-dipalmitoyloxypropyl]-Cys-Ser-Ser-Asn-Ala-OH; on silica gel: Rf (157)=0.55.

EXAMPLE 3

0.95 g of N-palmitoyl-S-[2(R),3-dipalmitoyloxypropyl]-Cys-Ser(Bu$^t$)-Ser(Bu$^t$)-OBu$^t$ is dissolved in 4 ml of 90% trifluoroacetic acid. After 15 minutes at 20°, there is added 100 ml of ether; the product obtained is filtered off, and the residue is dried over sodium hydroxide. The lipopeptide N-palmitoyl-S-[2(R),3-dipalmitoyloxypropyl]-Cys-Ser-Ser-OH is thus obtained as a colourless, non-hygroscopic powder; on silica gel: Rf (chloroform/methanol glacial acetic acid/water 79:25:0.5:4.5)=0.53.

EXAMPLE 4

The N-palmitoyl-S-[2(R),3-dihydroxypropyl]-(L)-cysteine used as starting material in Example 1 can be produced in the following manner:

13.9 g of N-palmitoyl-(L)-cysteine, 5.5 g of potassium carbonate and 15 g of 1-O-tosyl-2(R)-O-3-O-isopropylideneglycerol in 250 ml of ethanol are heated under nitrogen for 8 hours at 80°. After concentration by evaporation, the reaction mixture obtained is purified by chromatography on 400 g of silica gel Merck, by elution firstly with chloroform/acetone (8:2) and subsequently with chloroform/methanol (8:2). There is thus obtained the potassium salt of N-palmitoyl-S-[2(R),3-isopropylidenedioxypropyl]-(L)-cysteine, which is saponified by being heated for 4 hours at 80° in 80% aqueous acetic acid. The resulting product is evaporated to dryness; the residue is dissolved in chloroform and extracted with water. After drying and evaporating off the chloroform phase, there remains a colourless residue; this is recrystallised from cyclohexane to yield N-palmitoyl-S-[2(R),3-dihydroxypropyl]-(L)-cysteine, m.p. 110°, $[\alpha]_D^{20} = -25°$ (c=0.9, MeOH).

N-Palmitoyl-(L)-cysteine can be produced in the following manner:

45 g of (L)-cysteine (0.37 mole) is suspended in 350 ml of pyridine, and there is then added dropwise, with thorough stirring and in a nitrogen atmosphere, at room temperature a solution of 140 ml (1.67 equivalents) of palmitic acid chloride in 550 ml of methylene chloride. The reaction mixture is stirred for 20 hours; it is subsequently acidified with 2 N hydrochloric acid, and distributed between chloroform and water. The chloroform phase is dried and evaporated to dryness to yield a crystal mixture consisting to the extent of about a third of dipalmitoylcysteine and to the extent of about two thirds of monopalmitoylcysteine. Extraction is performed three times with 1 liter of hot acetone, from which crystallises a 1:1 mixture of di- and mono-palmitoyleysteine. From the acetone solution is obtained, by evaporating to dryness, N-palmitoyl-(L)-cysteine, which is recrystallised from ligroin; m.p. 65°–67°, $[\alpha]_D^{20} = -1°$ (c=0.8; methanol).

The mixtures of di- and mono-palmitoyl-(L)-cysteine are treated in a methanolic solution, with the addition of an aqueous solution of 12 g of sodium sulphide with 2 ml of conc. sodium hydroxide solution, for 15 minutes at room temperature. After evaporating off the methanol and acidifying the residue with 2 N hydrochloric acid there is obtained, by chloroform extraction, the remaining N-palmitoyl-(L)-cysteine, which is likewise recrystallised from ligroin.

EXAMPLE 5

0.80 g of N-palmitoyl-S-[2(R),3-dipalmitoyloxypropyl]-(L)-cysteine and 0.67 g of H-Ser(Bu$^t$)-Ser(Bu$^t$)-Phe-Ala-Glu(OBu$^t$)$_2$ are taken up in 10 ml of dimethylformamide, and 0.22 g of dicyclohexylcarbodiimide and 0.16 g of N-hydroxybenzotriazole are added. There is obtained by heating for a short time at 40° C. a clear solution which, after about one hour at 20°, solidifies into the form of a jelly. After 24 hours, this is again converted into a solution by heating at 40°, and from the solution obtained there is subsequently precipitated with water N-palmitoyl-S-[2(R),3-dipalmitoyloxypropyl]-Cys-Ser(Bu$^t$)-Ser(Bu$^t$)-Phe-Ala-Glu(OBu$^t$)$_2$. The product is purified by chromatography on silica gel in the system chloroform or chloroform/methanol 98:2, and gives the Rf value of 0.64 in chloroform/methanol/water 95:5.

540 mg of the compound thus obtained is dissolved in 30 ml of 90% trifluoroacetic acid, and the solution, after 30 minutes at 20°, is concentrated by evaporation to about a half, and N-palmitoyl-S-[2(R),3-dipalmitoyloxypropyl]-Cys-Ser-Ser-Phe-Ala-Glu-OH is precipitated with petroleum ether. The compound is centrifuged off, washed three times with petroleum ether, and dried over potassium hydroxide; the product obtained is a white powder having the Rf value (system 157) of 0.63.

The following lipopeptides are produced in an analogous manner:
N-palmitoyl-S-[2(R,S),3-dipalmitoyloxypropyl]-Cys-Phe-Phe-Asn-Ala-Lys-Oh, Rf (system 157 c)=0.18;
N-myristoyl-S-[2(R),3-dipalmitoyloxypropyl]-Cys-Glu-Gln-Asn-Ala-Lys-OH, Rf (system 157 c)=0.12;
N-lauroyl-S-[2(R),3-dipalmitoyloxypropyl]-Cys-Ser-Ser-Asn-Ala-Glu-OH, Rf (system 157 c)=0.20; and
N-stearoyl-S-[2(R),3-dipalmitoyloxypropyl]-Cys-Ser-Ser-Asn-Ala-Ala-OH, Rf The above described peptide provided with the stated protective groups, which peptide is used as starting material for the condensation reaction with N-palmitoyl-S-[2(R),3-dipalmitoyloxypropyl]-(L)-cysteine, can be produced in the following manner:

17.22 g of Z-Ala-ONp, 14.8 g of HCl.HGlu(OBu$^t$)$_2$ and 6.3 ml of N-ethylmorpholine in 40 ml of dimethylformamide are left to stand overnight at 20°. The solution is concentrated by evaporation, the residue is taken up in ethyl acetate, and extracted with 1 N sodium bicarbonate and water. The ethyl acetate solution is concentrated by evaporation, and it leaves, in the form of foam, Z-Ala-Glu(CBu$^t$)$_2$ having the Rf value of 0.60 (in chloroform/methanol 95:5), which is directly further processed: 8.5 g thereof is dissolved in 60 ml of methanol, and the solution, after the addition of 0.8 mg of Pd-charcoal (10%) is hydrogenated at 20° for 2 hours. The catalyst is filtered off, and the filtrate is concentrated by evaporation to yield H-Ala-Glu(OBu$^t$)$_2$ as a white foam giving the Rf value of 0.36 in chloroform/methanol 9:1.

To 11.46 g of Z-Phe-OH and 12.64 g of H-Ala-Glu(OBu$^t$)$_2$ in 50 ml of dimethylformamide are added at 0° 8.68 g of dicyclohexylcarbodiimide and 5.86 g of N-hydroxybenzotriazole. After standing for 15 hours at 4°, the resulting product is filtered off, the filtrate is concentrated by evaporation, and the residue is recrystallised from ethyl acetate/hexane. There is thus obtained Z-Phe-Ala-Glu(OBu$^t$)$_2$, m.p. 161°–163°; Rf (toluene/acetone 1:1)=0.63.

6.4 g of this product is dissolved in 50 ml of methanol and, after the addition of 0.5 g of Pd-charcoal (10%), the solution is hydrogenated at 20° for 20 minutes. The catalyst is filtered off, and the filtrate is concentrated by evaporation to yield H-Phe-Ala-Glu(OBu$^t$)$_2$ as white foam; Rf (chloroform/methanol 7:3)=0.75.

To 4.43 g of Z-Ser(Bu$^t$)-OH and 3.18 g of HCl.H-Ser(Bu$^t$)-OMe in 30 ml of dimethylformamide are added at 0° 1.89 ml of N-ethylmorpholine, 2.29 g of HOBt and 3.4 g of dicyclohexylcarbodiimide. After standing for 2 hours at 0° and for 15 hours at 20°, the resulting product is filtered off, the filtrate is concentrated by evaporation and taken up in ethyl acetate. After extraction of the solution with sodium bicarbonate, dilute hydrochloric acid and water, the solution is concentrated by evaporation to leave as oil Z-Ser(Bu$^t$)-Ser(Bu$^t$)-OMe; Rf (toluene/acetone 1:1)=0.70.

To a solution of 6.8 g of this product in 40 ml of methanol is added 7.5 ml of hydrazine hydrate, and after 24 hours at 20° the mixture is evaporated to about half the volume. It is then taken up in 250 ml of ethyl acetate, and extracted with water. The ethyl acetate solution is concentrated by evaporation and the Z-Ser(Bu$^t$)-Ser(Bu$^t$)-NH-NH$_2$ obtained is precipitated with petroleum ether; Rf (toluene/acetone 1:1)=0.50.

2.26 g of this product is dissolved in 20 ml of dimethylformamide, and at −10° are added 7.022 ml of 1.78 N HCl in ethyl acetate, and 0.635 ml of tert-butyl nitrite. After 10 minutes at −10°, there is added dropwise a solution of 2.38 g of H-Phe-Ala-Glu(OBu$^t$)$_2$ and 2.52 ml of N-ethylmorpholine, and the whole is allowed to stand for 1 hour at −10° and for 15 hours at 0°. The solution is then concentrated by evaporation; the residue is subsequently taken up in ethyl acetate, and washed with sodium bicarbonate, dilute hydrochloric acid and water. The solution is concentrated by evaporation to leave Z-Ser(Bu$^t$)-Ser(Bu$^t$)-Phe-Ala-Glu(OBu$^t$)$_2$, which is then recrystallised from ethyl acetate/hexane; m.p. 213°–215°, Rf (toluene/acetone 1:1)=0.70.

2.30 g of this product is dissolved in 40 ml of methanol and, after the addition of 0.5 g of Pd-charcoal (10%), the solution is hydrogenated at 20° for 2 hours. The catalyst is filtered off and the filtrate is concentrated by evaporation to yield H-Ser(Bu$^t$)-Ser(Bu$^t$)-Phe-Ala-Glu(OB$^t$)$_2$ in the form of a white foam; Rf (toluene/acetone 1:1)=0.23.

The N-palmitoyl-S-[2(R),3-dipalmitoyloxypropyl]-(L)-cysteine used as starting material and the diasteriomeric mixture of this compound with the corresponding 2(L) compound, which is denoted here in an abbreviated form as 2(R,S)$^n$, can be produced as follows:

6.3 g (2.78 mMols) of N-palmitoyl-S-[2(R),3-dipalmitoyloxypropyl]-(L)-cysteine-benzhydryl ester is dissolved in a mixture of 12 ml of trifluoroacetic acid and 48 ml of methylene chloride. After one hour at room temperature, the solution is concentrated by evaporation, and the oily residue is triturated with water. The N-palmitoyl-S-[2(R),3-dipalmitoyloxypropyl]-(L)-cysteine which has crystallised out is filtered off with suction, dried and, to remove the benzhydrol, triturated three times with ligroin. The residue is crystallised from acetone/water, and there are thus obtained colourless crystals of this product, m.p. 71°–75°; $[\alpha]_D^{20} = -1°$ (dioxane).

The above ester is obtained in the following manner:

12 g (20 mMols) of N-palmitoyl-S[2(R),3-dihydroxypropyl]-(L)-cysteine-benzhydryl ester is dissolved in a mixture of 60 ml of pyridine and 60 ml of methylene chloride, and there is then added dropwise at 0°–10° 14.5 ml (13.2 g) of palmitic acid chloride. After 2 hours at room temperature, the reaction has finished according to the thin-layer chromatogram. 10 ml of methanol is added to the suspension (pyridine hydrochloride); the reaction mixture is stirred for 20 minutes at 25°, and is then extensively concentrated by evaporation. The residue is taken up in chloroform; extraction is performed twice with 0.5 N hydrochloric acid, 10% sodium bicarbonate solution and water each time, the chloroform phase is dried with sodium sulphate, and subsequently evaporated to a syrup. The pure ester is obtained by chromatography of this syrup through silica gel in chloroform. The chromatographically homogeneous fractions (thin-layer chromatographical test on silica gel in chloroform:ethyl acetate 98:2, Rf=0.5) are concentrated by evaporation and recrystallised from acetone. There are thus obtained colourless crystals of N-palmitoyl-(S)-[2(R),3-dipalmitoyloxypropyl]-(L)-cysteinebenzhydryl ester, m.p. 69°–71°.

The benzylester of the N-palmitoyl-S[2(R),3-dihydroxypropyl]-(L)-cysteine used above is obtained, e.g., as follows:

23.4 g (54 mMols) of N-palmitoyl-S-[2(R),3-dihydroxypropyl]-(L)-cysteine is dissolved in 150 ml of a chloroform/ethanol mixture 1:1, and to this solution is added dropwise a solution of 13.6 g (70 mMols) of diphenyldiazomethane in 50 ml of chloroform. After 3 hours at room temperature, the initially red solution is decolorised and, according to thin-layer chromatography (chloroform:methanol=9:1, silica gel), the reaction is complete. The reaction mixture is concentrated in vacuo to dryness, and the residue is extracted cold with petroleum ether. The residue is filtered through silica gel with methylene chloride as solvent to thus obtain colourless crystals of benzhydryl ester, m.p. 88°–91°.

To produce N-palmitoyl-2-[2(R,S),3-dihydroxypropyl]-(L)-cysteine, the procedure is carried out as follows:

50 g (139 mMols) of N-palmitoyl-(L)-cysteine, 12,4 g of glycide and 45 g of potassium carbonate in 375 ml of ethanol are heated under nitrogen, with thorough stirring, for 16 hours at 80°. After cooling to room temperature, the reaction mixture is acidified with 2 N hydrochloric acid to about pH 4, and water is added; the product then precipitates. It is filtered off with suction, and washing with water is performed until the filtrate is free from chlorine ions. After drying the filter residue in vacuo, it is recrystallised from ethyl acetate to yield colourless crystals of the diastereoisomeric mixture of N-palmitoyl-S-[2(R),3-dihydroxypropyl]-(L)-cysteine and N-palmitoyl-S-[2(S),3-dihydroxypropyl]-(L)-cysteine, m.p. 76°-155°.

By reaction of N-palmitoyl-S-[2(R,S),3-dihydroxypropyl]-(L)-cysteine with diphenyldiazomethane, as described above for the R-compound, there is obtained N-palmitoyl-S-[2(R,S),3-dipalmitoyloxypropyl]-(L)-cysteinebenzhydryl ester: colourless crystals, m.p. 84°-85°.

If this diastereoisometric mixture (19.8 g) is chromatographed on a column with 250 g of silica gel (Merck) with methylene chloride as solvent, there is obtained in a first fraction 1.55 g of the R-diastereoisomer (Rf=0.61, methylene chloride/ethyl acetate=98:2, thin-layer, silica gel), in a second layer there is obtained 12.7 g of an R,S-diastereoisomeric mixture, and in a third fraction 1.1 g of the S-diastereoisomer (Rf=0.53 in methylene chloride/ethyl acetate=98:2).

From the (S)-diastereoisomer there is obtained, in the manner described above, N-palmitoyl-S-[2(S),3-dipalmitoyloxypropyl]-(L)-cysteine; colourless crystals, m.p. 64°-65° $[\alpha]_D^{20}= +1°$ (dioxane).

The starting materials required according to the invention for the production of the new lipopeptides which are mentioned in this Example and which are to be produced in a manner analogous to that in which N-palmitoyl-S[2(R),3-dipalmitoyloxypropyl]-Cys-Ser-Ser-Phe-Ala-Glu-OH is produced are, for example:

N-myristoyl-S-[2(R),3-dihydroxypropyl]-(L)-cysteine, colourless crystals, m.p. 140°-150°;

N-stearoyl-S-[2(R),3-dihydroxypropyl]-(L)-cysteine, colourless crystals, m.p. 140°-150°; and N-lauroyl-S-[2(R),3-dihydroxypropyl]-(L)-cysteine, colourless crystals, m.p. 140°-150°.

They can be produced according to the data given in Example 4.

The benzhydryl esters to be produced according to the information given above have the following characteristics:

N-myristoyl-S-[2(R),3-dihydroxypropyl]-(L)-cysteine-benzhydryl ester, colourless crystals, m.p. 90°-92°;

N-stearoyl-S-[2(R),3-dihydroxypropyl]-(L)-cysteine-benzhydryl ester, colourless crystals, m.p. 95°-97°; and N-lauroyl-S-[2(R),3-dihydroxypropyl]-(L)-cysteine-benzhydryl ester, colourless crystals, m.p. 95°-97°.

In a manner analogous to that described, it is possible to obtain the following N-acyl-S-[2(R),3-diacyloxypropyl]-(L)-cysteine-benzhydryl esters having various acyl groups on the N atom and on the O atom:

N-lauroyl-S-[2(R),3-dipalmitoyloxypropyl]-(L)-cysteine-benzhydryl ester, m.p. 65°-68°;

N-myristoyl-S-[2(R),3-dipalmitoyloxypropyl]-(L)-cysteine-benzhydryl ester, m.p. 68°-70°; and N-stearoyl-S-[2(R),3-dipalmitoyloxypropyl]-(L)-cysteine-benzhydryl ester, m.p. 70°-72°.

Further compounds which are to be used as intermediates and which can be produced according to the above data are:

N-lauroyl-S-[2(R),3-dipalmitoyloxypropyl]-(L)-cysteine, colourless crystals, m.p. 70°-72°;

N-myristoyl-S-[2(R),3-dipalmitoyloxypropyl]-(L)-cysteine, colourless crystals, m.p. 71°-73°; and N-stearoyl-S-[2(R),3-dipalmitoyloxypropyl]-(L)-cysteine, colourless crystals, m.p. 74°-77°.

EXAMPLE 6

By means of the reactions described in Example 5, there are produced the following starting materials for the production of lipopeptides according to the present application:

N-palmitoyl-S-[2(R),3-dilauroyloxypropyl]-(L)-cysteine-benzhydryl ester, colourless wax;

N-palmitoyl-S-[2(R),3-distearoyloxypropyl]-(L)-cysteine-benzhydryl ester, colourless crystals, m.p. 80°-82°;

N-palmitoyl-S-[2(R),3-dioleoyloxypropyl]-(L)-cysteine-benzhydryl ester, colourless oil;

N-palmitoyl-S-[2(R),3-dibehenoyloxypropyl]-(L)-cysteine-benzhydryl ester, colourless crystals, m.p. 85°-88°; and N-palmitoyl-S-[2(R),3-di-(dihydrosterkuloyloxypropyl]-(L)-cysteine-benzhydryl ester, colourless wax.

The corresponding unesterified substituted cysteines have the following characteristics:

N-palmitoyl-S-[2(R),3-dilauroyloxypropyl]-(L)-cysteine, colourless oil, Rf=0.27;

N-palmitoyl-S-[2(R),3-distearoyloxypropyl]-(L)-cysteine, colourless crystals, m.p. 82°-85°;

N-palmitoyl-S-[2(R),3-dioleoyloxypropyl]-(L)-cysteine, colourless oil, Rf in chloroform/methanol=9:1 (thin-layer silica gel (Merck))=0.35;

N-palmitolyl-S-[2(R),3-dibehenoyloxypropyl]-(L)-cysteine, colourless crystals, m.p. 87°-90; and N-palmitoyl-S-[2(R),3-di-(dihydrosterculoyloxypropyl]-(L)-cysteine, colourless wax, Rf=0.38 (identical conditions as given above for the N-palmitoyl-2,3-dioleoyloxy derivative).

These cysteine derivatives are condensed with the following peptides according to the data given in Example 5:

H-Phe-Phe-Asn-Ala-Lys-OH,
H-Glu-Gln-Asn-Ala-Lys-OH and
H-Ser-Ser-Asn-Ala-Glu-OH.

There are thus obtained the corresponding lipopeptides according to the invention.

EXAMPLE 7

0.9 g of N-palmitoyl-S-[2(R),3(R),4-trihydroxybutyl]-(L)-cysteine-benzhydryl ester in a mixture of 3 ml of trifluoroacetic acid and 12 ml of methylene chloride is allowed to stand for 2 hours at room temperature. The reaction mixture is then evaporated to dryness; the residue is triturated with ice-water, filtered off with suction and the solid substance is dried. It is then extracted with ligroin, and recrystallised from acetone to yield colourless crystals of N-palmitoyl-S-[2(R),3(R),4-trihydroxy-butyl]-(L)-cysteine, m.p. 76°-76.5°, having the specific rotation $[\alpha]_D^{20}= -5°$ (c=0.819, dioxane).

The benzhydryl ester used as starting material is obtained in the following manner:

1 g of N-palmitoyl-S-[2(R),3(R),4-trihydroxybutyl]-(L)-cysteine-benzhydryl ester is acylated in a mixture of 6 ml of pyridine in 5 ml of methylene chloride with 1.83 ml of palmitic acid chloride. After 18 hours at room temperature, there is added 1 ml of methanol, and the mixture is evaporated to dryness. The residue is filtered through 100 g of silica gel (Merck) with chloroform as solvent. The fractions that are pure according to thin-layer chromatography ($CHCl_3$:ethyl acetate=98:2) yield, after being concentrated by evaporation, colourless crystals, m.p. 60°-62°.

The starting material for the above reaction is obtained as follows:

2.53 g of N-palmitoyl-S-[2(R),3(R),4-trihydroxybutyl]-(L)-cysteine is reacted in a mixture of 12 ml of ethanol and 32 ml of chloroform with 1.37 g of diphenyldiazomethane for 15 hours at room temperature. The reaction mixture is subsequently evaporated to dryness, and the formed benzylhydryl ester is purified on 150 g of silica gel in chloroform as solvent; Rf=0.3 (CHCl$_3$:acetone=95:5) silica gel (Merck), thin layer.

N-Palmitoyl-S-[2(R),3(R),4-trihydroxybutyl]-(L)-cysteine is obtained in the following manner:

20 g of N-palmitoyl-(L)-cysteine, 27.6 g of 1-tosyl-2,4-ethylidene-D-erythrite and 17 g of potassium carbonate in 240 ml of ethanol are stirred under nitrogen for 15 hours at 80°. The salts are then filtered off, and the filtrate is evaporated to dryness. The residue is taken up in 200 ml of H$_2$O:tetrahydrofuran=1:1, and the solution is acidified with 2 N hydrochloric acid to pH=3. It is then extracted three times with ether; the pH value of the ether phase is adjusted with pyridine to 4.5; the ether phase is subsequently extracted with water, dried, and evaporated to dryness. This residue is purified through 200 g of silica gel (Merck) with chloroform:acetone=8:2 (1 l) and then with CHCl$_3$:MeOH=6:4 (1.2 l) as eluant.

The pure fractions are concentrated by evaporation, triturated with hexane and recrystallised from ethyl acetate/petroleum ether.

There are obtained colourless crystals of N-palmitoyl-S-[(2,4-ethylidene)-erythrityl]-(L)-cysteine, m.p. 62°–65°.

The hydrolysis of this compound is performed with 3% HBF$_4$ at 80° for 4.5 hours.

8.2 g of the ethylidene derivative is treated in 100 ml of dimethoxyethane and 100 ml of 3% HBF$_4$. The temperature is then lowered to 0°, whereupon the hydrolysis product precipitates. It is filtered off with suction, dried, and recrystallised from ethyl acetate, m.p. 160°–165°, sintering from 93°; Rf=0.285 (CHCl$_3$:MeOH=6:4), thin layer, silica gel (Merck).

EXAMPLE 8

By a procedure analogous to that given in Example 5, there are produced from N-stearoyl-S-[2(R),3-dipalmitoyloxypropyl]-(L)-cysteine and from N-palmitoyl-S-[2(R),3(R),4-tripalmitoyloxypropyl]-(L)-cysteine the following lipopeptides:

N-stearoyl-S-[2(R),3-dipalmitoyloxypropyl]-Cys-Ser-Ser-Asn-Ala-Glu-Ile-Asp-Glu-OH, Rf (157)=0.32;

N-palmitoyl-S-[2(R),3(R),4-tripalmitoyloxybutyl]-Cys-Ser-Ser-Asn-Ala-Lys-OH, Rf (157)=0.55; and N-palmitoyl-S-[2(R),3(R),4-tripalmitoyloxybutyl]-Cys-Ser-Ser-Asn-Ala-Lys-Ile-Asp-Glu-OH, Rf (157)=0.38.

EXAMPLE 9

In a manner analogous to that of Example 5, there are produced from N-palmitoyl-S-[2-(R),3-dipalmitoyloxypropyl]-(L)-cysteine or N-palmitoyl-S-[2(R,S), dipalmitoyloxypropyl]-(L)-cysteine the lipopeptides listed below; in this case the radicals of the cysteine derivatives just mentioned are denoted by PC(R) and PC(R,S), respectively:

PC(R,S)-Ser-Ser-Asn-OH
PC(R)-Ser-Ser-Asn-Ala-Lys-OH
PC(R,S)-Ser-Ser-Asn-Ala-Lys-OH
PC(R)-Ser-OH
PC(R,S)-Ser-OH
PC(R,S)-Ser-Ser-Asn-Ala-OH
PC(R)-Phe-Ile-Ile-Phe-Ala-OH
PC(R,S)-Phe-Ile-Ile-Phe-Ala-OH
PC(R)-Val-Lys-Val-Tyr-Pro-OH
PC(R,S)-Val-Lys-Val-Tyr-Pro-OH
PC(R)-Ala-Ile-Gly-Val-Gly-Ala-Pro-NH$_2$
PC(R,S)-Ala-Ile-Gly-Val-Gly-Ala-Pro-NH$_2$
PC(R)-Ser-Ser-Asn-Ala-Lys-Ile-Asp-Glu-OH
PC(R,S)-Ser-Ser-Asn-Ala-Lys-Ile-Asp-Glu-OH

Furthermore, there are produced the R,S-epimeric mixtures of all lipopeptides described in the preceding Examples.

EXAMPLE 10

0.24 g of N-palmitoyl-S-[2(R),3-dipalmitoyloxypropyl]-Cys-Ser (Bu$^t$)-Ser (Bu$^t$) -Phe-Ala-D.Glu(OBu$^t$)$_2$ are dissolved in 10 ml of trifluoracetic acid of 90% strength. The solution is evaporated after standing at 20° C. for 90 minutes, the residue is triturated with ether and then dried over sodium hydroxide. There is obtained N-palmitoyl-S-[2(R),3-dipalmitoyloxypropyl]-Cys-Ser-Ser-Phe-Ala-D.Glu-OH as a colorless, non hygroscopic powder. The Rf-value on silicagel (chloroform-methanol-water-acetic acid 75:25:5:0.5) is 0.37.

The starting material can be obtained in the following manner: 0.287 g of H-Phe-Ala-D.Glu(OBu$^t$)$_2$ is added to a mixture of 0.6 g of N-palmitoyl-S-[2(R),3-dipalmitoyloxypropyl]-Cys-Ser(Bu$^t$)-Ser(Bu$^t$)-OH, 0.092 g of N-hydroxybenzotriazole and 0.124 g of dicyclohexylcarbodiimide in 10 ml of methylene chloride. After standing for 24 hours at 20° the mixture is filtered and the filtrate chromatographed on a column (2×25 cm) of silicagel prepared in chloroform. Subsequent to an initial fraction of 25 ml, a main fraction containing pure N-palmitoyl-S-[2(R), 3-dipalmitoyloxypropyl]-Cys-Ser-(Bu$^t$)-Ser(Bu$^t$)-Phe-Ala-D.Glu(OBu$^t$)$_2$ is eluted with chloroform. The Rf-value on silicagel (chloroform-methanol 9:1) is 0.72.

4.75 ml of 1.12 M-tetrabutylammonium fluoride (Bu$_4$NF) in dimethylsulfoxide are added to a solution of 1.38 g of N-palmitoyl-S-[2(R), 3-dipalmitoyloxypropyl]-Cys-Ser(Bu$^t$)-Ser(Bu$^t$)-OTmse in 14 ml of dimethylformamide. After standing for 40 minutes at 20° the solution is poured on to 150 ml of ice-cold 0.01 N-hydrochloric acid, the mixture filtered and the residue washed with water until the filtrate no longer contains chloride ions and is then dried over sodium hydroxide. The N-palmitoyloxy-S-[2(R), 3-dipalmitoyloxypropyl]-Cys-Ser(Bu$^t$)-Ser(Bu$^t$)-OH is obtained in the form of a colorless powder. The Rf-value on silicagel (chloroform-methanol 9:1) is 0.20.

0.563 g of HCl.H-Ser(Bu$^t$)-Ser(Bu$^t$)-OTmse and 0.16 ml of N-ethylmorpholine are added to 1.06 g of N-palmitoyl-S-[2(R), 3-dipalmitoyloxypropyl]-L-cysteine, 0.213 g of N-hydroxybenzotriazole and 0.267 g of dicyclohexylcarbodiimide in 6 ml of dimethylformamide. After standing for 24 hours at 20° the solution has become gelatinous. This gelatin is dissolved on heating and the solvent is evaporated off on a rotary evaporator. The residue is chromatographed on a column of silicagel which has been prepared in chloroform. Pure N-palmitoyl-S-[2(R), 3-dipalmitoxypropyl]-Cys-Ser (Bu$^t$)-Ser(Bu$^t$)-OTmse is eluted with chloroform-methanol 99:1. The Rf-value (ethyl acetate-petroleum-ether 1:1) on silicagel is 0.62. 5.39 g of Z-Ser(Bu$^t$)-Ser(-Bu$^t$)-OTmse are hydrogenated in methanol for 2 hours at pH 4.5 (adjusting it continuously with 1 N-hydrochloric acid) in the presence of 0.6 g of palladium-carbon catalyst (10%). After having filtered off the catalyst and evaporated the filtrate a white foam representing HCl.H-Ser(Bu$^t$)-Ser(Bu$^t$)-OTmse is obtained. The Rf-value on silicagel (chloroform-methanol) 9:1 is 0.57. 7.0 g of HCl.H-Ser(Bu$^t$)-OTmse and 2.96 ml of N-ethylmorpholine are added to 6.94 g of Z-Ser(Bu$^t$)-OH, 3.6 g of N-hydroxybenzotriazole and 5.33 g of dicyclohexylcarbodiimide in 100 ml of dimethylformamide. After standing 1 hour at 0° and 24 hours at 20° the mixture is filtered, the residue is taken up in ethyl acetate and the solution is washed with 1 N-citric acid, 1 N-sodium bicarbonate and water. After drying over sodium sulfate the solvent is evaporated off and an oil representing Z-Ser(Bu$^t$)-Ser(Bu$^t$)-OTmse is obtained. The Rf-value on silicagel (ethyl acetate-petroleum ether 1:1) is 0.69.

1.84 g of Z-Phe-Ala-D.Glu(OBu$^t$)$_2$ are hydrogenated in 50 ml of methanol in the presence of 0.25 g of palladium carbon (10%). After filtering off the catalyst and evaporating the filtrate the peptide H-Phe-Ala-D.Glu(OBu$^t$)$_2$ is obtained as a white foam. The Rf-value on silicagel (chloroform-methanol 8:2) is 0.58.

3.08 g of H-Ala-D.Glu(OBu$^t$)$_2$ is added to 2.79 g of Z-Phe-OH, 1.57 g of N-hydroxybenzotriazole and 2.31 g of dicyclohexylcarbodiimide in 60 ml of dimethylformamide. After standing at 0° for 20 hours the batch is filtered, the filtrate is freed from the solvent, the residue is taken up in ethyl acetate and the solution is extracted with 1 N-citric acid, 1 N-sodium bicarbonate and water. After drying over sodium sulfate the solvent is evaporated off and the residue is precipitated from ethyl acetate-petroleum ether. A colorless powder representing Z-Phe-Ala-D.Glu(OBu$^t$)$_2$ is obtained. The Rf-value on silicagel (in chloroform-methanol 9:1) is 0.75.

4.33 g of Z-Ala-D.Glu(OBu$^t$)$_2$ are hydrogenated in 50 ml of methanol in the presence of 0.5 g of palladium-carbon (10%). After having filtered off the catalyst and evaporated the filtrate H-Ala-Glu(OBu$^t$)$_2$ is obtained as a white foam. The Rf-value on silicagel in the system chloroform-methanol 9:1 is 0.30.

2.96 g of HCL.H-D.Glu(OBu$^t$)$_2$ and 1.27 ml of N-ethyl morpholine are added to 2.23 g of Z-Ala-OH, 1.68 g of N-hydroxybenzotriazole and 2.48 g of dicyclohexylcarbodiimide in 50 ml of dimethyl formamide. After standing for 24 hours at 0° the mixture is filtered and the solvent is removed from the filtrate by evaporation. By recrystallizing the residue from ethyl-acetate-hexane Z-Ala-D.Glu(OBu$^t$)$_2$ melting at 99°–101° and having the optical rotation $[\alpha]_D = +5°$ (c=1.4 in methanol) is obtained.

EXAMPLE 11

2.48 g of N-palmitoyl-S-[2(R), 3-dipalmitoyloxypropyl]-Cys-Ser(Bu$^t$)-Ser(Bu$^t$)-Asn-Ala-Lys (Boc)-NH$_2$ are dissolved in 50 ml of trifluoroacetic acid of 90% strength. After standing for 60 minutes at 20° the solution is freed from the solvent by evaporation and the residue is dried over sodium hydroxide. The product is then taken up in 2 ml of dimethylformamide and precipitated therefrom with 200 ml of 5%—aqueous sodium bicarbonate solution, filtered and washed with water. There is obtained a colorless powder representing N-palmitoyl-S-[2(R), 3-dipalmitoyloxypropyl]-Cys-Ser-Ser-Asn-Ala-Lys-NH$_2$ having an Rf-value of 0.40 on silicagel in the system 157.

1.64 g of H-Ser(Bu$^t$)-Ser(Bu$^t$)-Asn-Ala-Lys(Boc)-NH$_2$ is added to 2.0 g of N-palmitoyl-S-[2(R), 3-dipalmitoyloxypropyl]-L-cysteine, 0.404 g of N-hydroxybenzotriazole and 0.544 g of dicyclohexylcarbodiimide in 50 ml of methylene chloride. After standing at 20° for 24 hours the solvent is evaporated off and the residue is purified by chromatography on a column of silicagel (prepared in chloroform). After an initial fraction consisting of chloroform, a fraction is obtained on elution with chloroform-methanol 98:2 containing pure N-palmitoyl-S-[2(R), 3-dipalmitoyloxypropyl]-Cys-Ser(Bu$^t$)-Ser(Bu$^t$)-Asn-Ala-Lys(Boc)-NH$_2$. The Rf-value on silicagel in chloroform-methanol 9:1 is 0.38.

1.275 g of Z-Ser(Bu$^t$)-Ser(Bu$^t$)-Asn-Ala-Lys(Boc)-NH$_2$ are hydrogenated in 50 ml of methanol in the presence of 0.25 g of palladium-carbon catalyst (10%). After filtering off the catalyst and evaporating off the solvent in the filtrate there is obtained a white foam consisting of n-Ser(Bu$^t$)-Ser(Bu$^t$)-Asn-Ala-Lys(Boc)-NH$_2$. The Rf-value on silicagel in the system chloroform-methanol 8:2 is 0.20.

2.02 g of HCl.H.Lys(Boc)-NH$_2$ and 0.902 ml of N-ethylmorpholine are added to 4.465 g of Z-Ser(Bu$^t$)-Ser(Bu$^t$)-Asn-Ala-CH, 1.095 g of N-hydroxybenzotriazole and 1.622 g of dicyclohexylcarbodiimide in 50 ml of dimethylformamide. After 24 hours the mixture is filtered and the reaction product is precipitated from the filtrate with water and then recrystallized from methanol-ether. The melting point is 207°–208°.

34 ml of 0.5 N-sodium hydroxide is added to 3.54 g of Z-Ser(Bu$^t$)Ser(Bu$^t$)-Asn-Ala-OMe in 34 ml of methanol. After 3 minutes 17 ml of 1 N-hydrochloric acid is added, the methanol is removed by evaporation for the most part and the product which has separated out is filtered. By crystallization from methanol-ether there is obtained pure Z-Ser(Bu$^t$)-Ser(Bu$^t$)-Asn-Ala-OH of melting point 180°–181°.

61.8 ml of 2.32 N-hydrochloric acid in ethyl acetate and 7.3 ml of tert.butyl nitrite are added to 25.95 g of Z-Ser(Bu$^t$)-Ser(Bu$^t$)-NH-NH$_2$ in 200 ml of dimethylformamide at $-10°$. After 10 minutes a solution of 14.8 g of HCl.H-Asn-Ala-OMe and 36.16 ml of N-ethyl morpholine in 150 ml of dimethylformamide is added dropwise and the mixture is then kept for one hour at $-10°$ and 15 hours at 0°. The solution is freed from the solvent by evaporation, the residue is taken up in chloroform and washed with sodium bicarbonate, dilute hydrochloric acid and with water. The Z-Ser(Bu$^t$)-Ser(Bu$^t$)-Asn-Ala-OCH$_3$ obtained after evaporation of the solvent is reprecipitated from chloroform-petroleum ether. The Rf-value on silicagel in the system chloroform-methanol 9:1 is 0.35.

20.15 g of Z-Asn-Ala-OMe are hydrogenated in 500 ml of methanol in the presence of 2.0 g of palladium carbon catalyst (10%) at pH 4.5 (the pH is kept at this value by continuously adding 1-N-hydrochloric acid). After having filtered the catalyst and evaporated the filtrate a white powder is obtained consisting of HCl.Asn-Ala-O-CH$_3$. The Rf-value in chloroform-methanol-water 70:30:5 on silicagel is 0.25.

EXAMPLE 12

The following lipopeptides are prepared by a process substantially equivalent to that of Example 5:
N-palmitoyl-S-[2(R,S), 3-dipalmitoyloxypropyl]-Cys-Ser-Ser-Asn-Ala-Glu-OH, Rf (157)=0.65.
N-palmitoyl-S-[2(R,S), 3-dipalmitoyloxypropyl]-Cys-Ser-Ser-Asn-Ala-Ala-OH.
N-palmitoyl-S-[2(R,S),3-dipalmitoloxypropyl]-Cys-Phe-Ile-Ile-Phe-Ala-OCH$_3$, Rf (157)=0.43.
N-palmitoyl-S-[2(S), 3-dipalmitoyloxypropyl]-Cys-Ser-Ser-Phe-Ala-Glu-OH, Rf (157)=0.63.

N-palmitoyl-S-[2(R,S), 3-dipalmitoyloxypropyl]-Cys-Ser-Thr-Ala-Glu-OH, Rf (157c)=0.37.
N-palmitoyl-S-[2(R,S), 3-dipalmitoyloxypropyl]-Cys-Thr-Ser-Phe-Ala-Glu-OH, Rf (157c)=0.35.
N-palmitoyl-S-[2(R,S)-dipalmitoyloxypropyl]-Cys-Thr-Thr-Phe-Ala-Glu-OH, Rf (157c)=0.37.
N-palmitoyl-S-[2(R)-dipalmitoyloxypropyl]-Cys-Ser-Ser-PHe-Ala-D.Glu-OH,
N-palmitoyl-S-[2(R), 3-diastearoyloxypropyl]-Cys-Ser-Ser-Asn-Ala-D.Glu-OH.
N-palmitoyl-S-[2(R,S),-3-dipalmitoyloxypropyl]-Cys-Ser-Ser-Ala-Glu-OH
N-palmitoyl-S-[2(R,S), 3-dipalmitoyloxypropyl]-Cys-Glu-Glu-Asn-Ala-Lys-OH.

EXAMPLE 13

The following lipopeptides are prepared by a process substantially equivalent to that of Example 5:
N-palmitoyl-S-[2(R), 3-dilauroyloxypropyl]-Cys-Ser-Ser-Phe-Ala-Glu-OH Rf (157)=0.45.
N-palmitoyl-S-[2(R), 3-dimyristoyloxypropyl]-Cys-Ser-Ser-Phe-Ala-Glu-OH, Rf (157)=0.47.
N-palmitoyl-S-[2(R), 3-distearoyloxypropyl]-Cys-Ser-Ser-Phe-Ala-Glu-OH, Rf (157)=0.50.
N-palmitoyl-S-[2(R), 3-dioleoyloxypropyl]-Cys-Ser-Ser-Phe-Ala-Glu-OH, Rf (157)=0.53.
N-palmitoyl-S-[2(R), 3-di(9-methylene-stearoyloxypropyl)]-Cys-Ser-Ser-Phe-Ala-Glu-OH, Rf (157)=0.53.

EXAMPLE 14

0,185 g of dicyclohexylcarbodiimide, 0,1 g of N-hydroxy-benzotriazole and 0.105 ml of N-ethyl morpholine are added to 0.749 g of N-palmitoyl-S-[2(R), 3-dipalmitoyloxypropyl]-Cys-Ser-OH and 0.30 g of HCl.H-Phe-Tyr-NH$_2$ in 15 ml of methylene chloride. After standing for 24 hours at 20° the mixture is filtered, the filtrate evaporated and the residue triturated twice with 10 ml of water each time. The residue is then taken up in 15 ml of chloroform and chromatographed on a silicagel-column (2×25 cm) which has been prepared in chloroform.

After an initial fraction of 25 ml (chloroform as eluant) the pure N-palmitoyl-S[2(R), 3-dipalmitoyloxypropyl]-Cys-Ser-Phe-Tyr-NH$_2$ is eluted with chloroform-methanol. Rf on silicagel (chloroform-methanol 9:1)=0.48.

The hydrochloride named above can be prepared in the following manner: 4.62 g of Z-Phe-Tyr-NH$_2$ are hydrogenated in 50 ml of methanol in the presence of 4 ml of hydrochloric acid in methanol (2.53 N) and 0.5 g of palladium-carbon (10%). After filtering the catalyst and evaporating the filtrate the HCl.H-Phe-Tyr-NH$_2$ is obtained as a white foam. Rf-value on silicagel (with chloroform-methanol) is 0.42.

2.52 ml of N-ethylmorpholine are added to 7.93 g of Z-Phe-O-Su and 4.33 g of HCl.H-Tyr-NH$_2$ in 50 ml of dimethylformamide. After standing for 20 hours at 20° the solution is concentrated to about the half volume and the reaction product is precipitated by the addition of 200 ml of water. The residue is filtered and recrystallized from hot acetonitrile. The melting point of the so obtained Z-Phe-Tyr-NH$_2$ is 221°–223°; [α]$_D$= −25° (c=0.5 in methanol).

EXAMPLE 15

1.25 g N-palmitoyl-S-[2(R),3-dihexadecyloxypropyl]-Cys-Ser(Bu$^t$)-Ser(Bu$^t$)-Phe-Ala-Glu(OBu$^t$)$_2$ are added to 15 ml of 90% trifluoroacetic acid and the solution is allowed to stand for 60 minutes and then evaporated. The residue is digested with 5 ml of ethyl acetate and then dried over potassium hydroxide. The so obtained lipopeptide N-palmitoyl-S-[2(R),3-dihexadecyloxypropyl]-Cys-Ser-Ser-Phe-Ala-Glu-OH has an Rf value of 0.32 (157c) in the thin layer chromatogram on silicagel.

The above starting compound can be obtained as follows: 0.475 g of dicyclohexylcarbodiimide and 0,355 g of N-hydroxybenzotriazole are added to 1.7 g of N-palmitoyl-S-[2(R),3-dihexadecyloxypropyl]-(L)-cysteine and 1.47 g of H-Ser(Bu$^t$)-Ser(Bu$^t$)-Phe-Ala-Glu(OBu$^t$)$_2$ in 25 ml of dimethylformamide. After standing for 20 hours at 20° the solvent is evaporated off under reduced pressure and the residue is purified by chromatography on a column of silicagel. N-palmitoyl-S-[2(R),3-dihexadecyloxypropyl]-Cys-Ser(Bu$^t$)-Ser(-Bu$^t$)-Phe-Ala-Glu(OBu$^t$)$_2$ having an Rf value 0.63 (chloroform-methanol 95:5) in the thin layer chromatogram on silicagel is eluted with chloroform-methanol (99:1).

EXAMPLE 16

0.95 g of N-palmitoyl-S-[2(R,S)-hydroxyoctadecyl]-Cys-Ser(Bu$^t$)-Ser(Bu$^t$)-Phe-Ala-Glu(OBu$^t$)$_2$ is added to 10 ml of 90% trifluoroacetic acid and the solution is evaporated at 20° under reduced pressure after 45 minutes. The residue is digested in water and dried over potassium hydroxide. The pure N-palmitoyl-S-[2(R,S)-hydroxyoctadecyl]-Cys-Ser-Ser-Phe-Ala-Glu-OH is obtained which has an Rf-value of 0.35 (157) in the thin layer chromatogram on silicagel.

The above starting material is obtained in a manner analogous to that described in Example 15 by condensing N-palmitoyl-S-[2(R,S)-hydroxyoctadecyl]-(L)-cysteine with H-Ser-(Bu$^t$)-Ser(Bu$^t$)-Phe-Ala-Glu(OBu$^t$)$_2$. The Rf value in the thin layer chromatogram (chloroform-methanol 98:2) on silicagel is 0.13. In the system 157A the value is 0.60.

EXAMPLE 17

1.1 g of N-palmitoyl-S-[2(R,S)-palmitoyloxyoctadecyl]-Cys-Ser(Bu$^t$)-Ser(Bu$^t$)-Phe-Ala-Glu(OBu$^t$)$_2$ are added to 15 ml of 90% trifluoroacetic acid and the mixture is evaporated at 20° after 60 min. The residue is digested with ethyl acetate and then dried over potassium hydroxide. The N-palmitoyl-S-[2(R,S)-palmitoyloxy-octadecyl]-Cys-Ser-Ser-Phe-Ala-Glu-OH is obtained showing an Rf value of 0.44 in the thin layer chromatogram on silicagel (157).

The starting material can be obtained as follows:
0.32 g N-hydroxybenzotriazole and 0.37 g of dicyclohexylcarbodiimide are added to 1.3 g of N-palmitoyl-S-[2(R,S)-palmitoyloxyoctadecyl]-(L)-cysteine and 1.5 g of H-Ser(Bu$^t$)-Ser(Bu$^t$)-Phe-Ala-Glu(OBu$^t$)$_2$ in 25 ml of dimethylformamide. After standing for 15 hours at room temperature the solvent is evaporated off under reduced pressure and the residue is purified by chromatography on a column of silicagel. N-palmitoyl-S-[2(R,S)-palmitoyloxyoctadecyl]-Cys-Ser-(Bu$^t$)-Ser(-Bu$^t$)-Phe-Ala-Glu(OBu$^t$)$_2$ is eluted with chloroform-methanol 98:2 having an Rf value of 0.48 in the system chloroform methanol 95:5 and of 0.74 in the system 157 A in the thin layer chromatogram on silicagel.

EXAMPLE 18

0.98 g of N-palmitoyl-S-octadecyl-Cys-Ser(Bu$^t$)-Ser(Bu$^t$)-Phe-Ala-D-Glu(OBu$^t$)$_2$ are added to 10 ml of 90% trifluoroacetic acid. The solution is evaporated after 50 minutes standing at 20° under reduced pressure and the residue is dried over potassium hydroxide. The N-palmitoyl-S-octadecyl-Cys-Ser-Ser-Ala-D-Glu-OH is obtained having in the thin layer chromatogram on silicagel an Rf value 0.43 (157c).

The starting materials can be obtained as follows:

0.5 g of dicyclohexylcarbodiimide and 0.37 g of N-hydroxybenzotriazole are added to 1.22 g of N-palmitoyl-S-octadecyl-(L)-cysteine and 1.53 g of H-Ser(Bu$^t$)-Ser(Bu$^t$)-Phe-Ala-D-Glu(OBu$^t$)$_2$ in 25 ml of dimethylformamide. After 20 hours the reaction mixture is evaporated under reduced pressure and the residue is purified by chromatography on a column of silicagel. The N-palmitoyl-S-octadecyl-Cys-Ser(Bu$^t$)-Ser(Bu$^t$)-Phe-Ala-D-Glu(OBu$^t$)$_2$ is eluted with chloroform-methanol 97:3. The Rf value in the thin layer chromatogram silicagel is 0.80 (chloroform-methanol 9:1).

0.2 g of 10% palladium on carbon are added to 1.84 g of Z-Phe-Ala-D-Glu(OBu$^t$)$_2$, in 50 ml of methanol, and the mixture is hydrogenated for 3 hours. The catalyst is filtered off and the filtrate is evaporated. The so obtained H-Phe-Ala-D-Clu(OBu$^t$)$_2$ has an Rf value in the thin layer chromatogram of 0.60 (chloroform-methanol 8:2).

2.31 g of dicyclohexylcarbodiimide and 1.57 g of N-hydroxybenzotriazole are added at 0° to 2.79 g og Z-Phe-OH and 3.08 g of H-Ala-D Glu(OBu$^t$)$_2$ in 60 ml of dimethylformamide. After 20 hours standing at room temperature mixture is filtered and the filtrate evaporated. The residue is taken up in 200 ml of ethyl acetate and the solution is extracted with 1 N citric acid, 1 N sodium bicarbonate and water.

After having dried the solution with sodium sulfate it is evaporated and the residue is precipitated from methanol and ether. Z-Phe-Ala-D-Glu(OBu$^t$)$_2$ is obtained having an Rf value of 0.80 in the thin layer chromatogram on silicagel (chloroform-methanol 8:2).

4.33 g of Z-Ala-D-Glu(OBu$^t$)$_2$ are dissolved in 45 ml of methanol and hydrogenated for one hour at room temperature after having added 0.4 g of 10% palladium on carbon. The catalyst is then filtered off and the solvent evaporated. The H-Ala-D-Glu(OBu$^t$)$_2$ obtained as residue shows an Rf value of 0.24 in the thin layer chromatogram on silicagel (chloroform-methanol 9:1). 1.27 ml of N-ethyl-morpholine, 2.46 g of dicyclohexylcarbodiimide and 1.68 g of N-hydroxybenzotriazole are added to 2.23 g of Z-Ala-OH and 2.96 g of HCl.H-D-Glu(OBu$^t$)$_2$ in 50 ml of dimethyl formamide at 0°. After standing for 15 hours at 4° the mixture is filtered, the filtrate is evaporated and the residue is dissolved in ethyl acetate. The solution is extracted with 1 N citric acid, 1 N sodium bicarbonate and water and dried over sodium sulfate. After evaporating the solvent there is obtained Z-Ala-D-Glu(OBu$^t$)$_2$ which is precipitated from ethyl acetate and petroleum ether. The Rf-value is the thin layer chromatogram on silicagel (chloroform-methanol 9:1) is 0.72.

3.29 ml of 2.28 N HCl in ethyl acetate and 0.381 ml of tertiary butyl nitrite are added to 1.36 g of Z-Ser(Bu$^t$)-Ser(Bu$^t$)-NR-NH$_2$ in 15 ml of dimethylformamide at −15°. After 10 minutes at −10° a solution of 1.44 g of H-Phe-Ala-D-Glu(OBu$^t$)$_2$ and 1.5 ml of N-ethylmorpholine in 10 ml of dimethylformamide are added. The mixture is allowed to react for one hour at −10° and for 15 hours at 0°. The solution is then evaporated, the residue is taken up in ethyl acetate and this solution is extracted with 1 N citric acid, 1 N sodium bicarbonate and water, dried over sodium sulfate and evaporated. The Z-Ser-(Bu$^t$)-Ser(Bu$^t$)-Phe-Ala-D-Glu(OBu$^t$)$_2$ is recrystallized from ethyl acetate-hexane. It melts at 205°–209°. $[\alpha]_D = -4°$ (c=0.6 in CHCl$_3$).

2.3 g of this product are dissolved in 40 ml of methanol and after having added 0.5 g of 10% palladium on carbon hydrogenated at 20° for 2 hours. The catalyst is filtered off and the filtrate evaporated. The H-Ser(Bu$^t$)-Ser(Bu$^t$)-Phe-Ala-D-Glu(OBu$^t$)$_2$ is obtained as a white foam. The Rf value is chloroform-methanol 9:1 is 0.47.

H-Ser(Bu$^t$)-Ser(Bu$^t$)-Asn-Ala-D-Glu(OBu$^t$)$_2$ is prepared in analogous manner. The Rf value in thin layer chromatography on silicagel is 0.48 (chloroform-methanol 8:2).

Z-Ser(Bu$^t$)-Ser(Bu$^t$)-Asn-Ala-D-Glu(OBu$^t$)$_2$: Melting point 168°–170°. $[\alpha]_D = -6°$ (c=0.8 in CH$_3$OH).

EXAMPLE 19

1.4 g of N-palmitoyl-S-[2R,3-dihexadecyloxypropyl]-(D,L)-homocysteinyl-Ser(Bu$^t$)-Ser(Bu$^t$)-Asn-Ala-Glu(OBu$^t$)$_2$ are added to 15 ml of 90% trifluoroacetic acid and after 50 minutes the mixture is freed from the solvent by evaporation. The residue is dried over potassium hydroxide. N-palmitoyl-S-[2R,3-dihexadecyloxypropyl]-(D,L)-homocysteinyl-Ser-Ser-Asn-Ala-Glu-OH is obtained as a wax. The starting compound can be obtained according to the method described in the Examples 15–18 from N-palmitoyl-S-[2R,3-dihexadecyloxypropyl]-(D,L)-homocysteine and H-Ser(Bu$^t$)-Ser(Bu$^t$)-Asn-Ala-Glu(OBu$^t$)$_2$.

EXAMPLE 20

1.2 g of N,S-dipalmitoyl-(L)-cysteinyl-Ser(Bu$^t$)-Ser(-Bu)-Phe-Ala-Glu(OBu$^t$)$_2$ are added to 15 ml of 90% trifluoroacetic acid and allowed to react for 45 minutes. After evaporating the trifluoroacetic acid there is obtained [N,S-dipalmitoyl]-Cys-Ser-Ser-Phe-Ala-Glu-OH.

The starting material is obtained following the methods set forth in the Examples 15–18 from N,S-dipalmitoyl-cysteine and H-Ser(Bu$^t$)-Ser(Bu$^t$)-Phe-Ala-Glu(OBu$^t$)$_2$.

EXAMPLE 21

Starting from the N-palmitoyl-S-[2(R),3-dihexadecyloxypropyl]-(L)-cysteine, N-palmitoyl-S-[2(R,S)-hydroxy-octadecyl]-(L)-cysteine, N-palmitoyl-S-[2(R,S)-palmitoyloxy-octacedyl]-(L)-cysteine, N-palmitoyl-S-octadecyl-(L)-cysteine, N-palmitoyl-S-[2R,3-dihexadecyloxypropyl]-(D,L)-homocysteine, N,S-dipalmitoyl-L-cysteine, N-palmitoyl-S-[2(R,S)-palmitoyloxy-eicosanyl]-(L)-cysteine and which are designated hereafter by the abbreviations C$_1$CH, C$_2$OH, C$_3$OH, C$_4$OH, C$_5$OH, C$_6$OH and C$_7$OH, the OH group indicating the carboxyl function of the substituted cysteine, and condensing each of these compounds with the peptides set forth below, using the protecting groups as in Examples 15–18 and using the same methods H-Ser-Ser-D-Asn-Ala-Glu-OH
H-Thr-Thr-Asn-Ala-Lys-OH
H-Ser-Thr-Asn-D-Ala-Lys-OH
H-Ser-Ser-Asn-Ala-Glu-OH
H-Thr-Ser-Phe-Ala-D-Glu-OH
H-Ser-Ser-Phe-Ala-D-Glu-OH H-Ser-Ser-Phe-Ala-Glu-OH
H-D-Ser-D-Ser-D-Phe-Ala-D-Glu-OH
H-D-Thr-D-Phe-D-Ala-D-Glu-OH
there are obtained the following lipopeptides:
$C_1$-Ser-Ser-D-Asn-Ala-Glu-OH
$C_1$-Thr-Thr-Asn-Ala-Lys-OH
$C_1$-Ser-Thr-Asn-D-Ala-Lys-OH
$C_1$-Ser-Ser-Asn-Ala-Glu-OH
$C_1$-Thr-Ser-Phe-Ala-D-Glu-OH
$C_1$-Ser-Ser-Phe-Ala-D-Glu-OH
$C_1$-Ser-Ser-Phe-Ala-Glu-OH
$C_1$-D-Ser-D-Ser-D-Phe-Ala-D-Glu-OH
$C_1$-D-Thr-D-Phe-D-Ala-D-Glu-OH
$C_2$-Ser-Ser-D-Asn-Ala-Glu-OH
$C_2$-Thr-Thr-Asn-Ala-Lys-OH
$C_2$-Ser-Thr-Asn-D-Ala-Lys-OH
$C_2$-Ser-Ser-Asn-Ala-Glu-OH
$C_2$-Thr-Ser-Phe-Ala-D-Glu-OH
$C_2$-Ser-Ser-Phe-Ala-D-Glu-OH
$C_2$-Ser-Ser-Phe-Ala-Glu-OH
$C_2$-D-Ser-D-Ser-D-Phe-Ala-D-Glu-OH
$C_2$-D-Thr-D-Phe-D-Ala-D-Glu-OH
$C_3$-Ser-Ser-D-Asn-Ala-Glu-OH
$C_3$Thr-Thr-Asn-Ala-Lys-OH
$C_3$-Ser-Thr-Asn-D-Ala-Lys-OH
$C_3$-Ser-Ser-Asn-Ala-Glu-OH
$C_3$-Thr-Ser-Phe-Ala-D-Glu-OH
$C_3$-Ser-Ser-Phe-Ala-D-Glu-OH
$C_3$-Ser-Ser-Phe-Ala-Glu-OH
$C_3$-D-Ser-D-Ser-D-Phe-Ala-D-Glu-OH
$C_3$-D-Thr-D-Phe-D-Ala-D-Glu-OH
$C_4$-Ser-Ser-D-Asn-Ala-Glu-OH
$C_4$-Thr-Thr-Asn-Ala-Lys-OH
$C_4$-Ser-Thr-Asn-D-Ala-Lys-OH
$C_4$-Ser-Ser-Asn-Ala-Glu-OH
$C_4$-Thr-Ser-Phe-Ala-D-Glu-OH
$C_4$-Ser-Ser-Phe-Ala-D-Glu-OH
$C_4$-Ser-Ser-Phe-Ala-Glu-OH
$C_4$-D-Ser-D-Ser-D-Phe-Ala-D-Glu-OH
$C_4$-D-Thr-D-Phe-D-Ala-D-Glu-OH
$C_5$-Ser-Ser-D-Asn-Ala-Glu-OH
$C_5$-Thr-Thr-Asn-Ala-Lys-OH
$C_5$-Ser-Thr-Asn-D-Ala-Lys-OH
$C_5$-Ser-Ser-Asn-Ala-Glu-OH
$C_5$-Thr-Ser-Phe-Ala-D-Glu-OH
$C_5$-Ser-Ser-Phe-Ala-D-Glu-OH
$C_5$-Ser-Ser-Phe-Ala-Glu-OH
$C_5$-D-Ser-D-Ser-D-Phe-Ala-D-Glu-OH
$C_5$-D-Thr-D-Phe-D-Ala-D-Glu-OH
$C_6$-Ser-Ser-D-Asn-Ala-Glu-OH
$C_6$-Thr-Thr-Asn-Ala-Lys-OH
$C_6$-Ser-Thr-Asn-D-Ala-Lys-OH
$C_6$-Ser-Ser-Asn-Ala-Glu-OH
$C_6$-Thr-Ser-Phe-Ala-D-Glu-OH
$C_6$-Ser-Ser-Phe-Ala-D-Glu-OH
$C_6$-Ser-Ser-Phe-Ala-Glu-OH
$C_6$-D-Ser-D-Ser-D-Phe-Ala-D-Glu-OH
$C_6$-D-Thr-D-Phe-D-Ala-D-Glu-OH
$C_7$-Ser-Ser-D-Asn-Ala-Glu-OH
$C_7$-Thr-Thr-Asn-Ala-Lys-OH
$C_7$-Ser-Thr-Asn-D-Ala-Lys-OH
$C_7$-Ser-Ser-Asn-Ala-Glu-OH
$C_7$-Thr-Ser-Phe-Ala-D-Glu-OH
$C_7$-Ser-Ser-Phe-Ala-D-Glu-OH
$C_7$-Ser-Ser-Phe-Ala-Glu-OH
$C_7$-D-Ser-D-Ser-D-Phe-Ala-D-Glu-OH
$C_7$-D-Thr-D-Phe-D-Ala-D-Glu-OH

EXAMPLE 22

The cysteines mentioned in the preceding or following Examples to be used as starting materials may be prepared as follows:

189 mg of N-palmitoyl-(L)-cysteine are added to 41.5 mg of sodium hydride dispersion in about 5 ml of absolute dioxane and allowed to react at 0° under a nitrogen atmosphere until the evolution of hydrogen has ceased. 330 mg of 1-tosyl-[2(R),3-dihexadecyl]-glycetine in 2 ml of dioxane are added and the whole is heated at 90° for 15 hours. After evaporation of the solvents the residue is acidified with 1 N HCl to a pH of about 3 and is distributed between chloroform and water. The chloroform phase is dried and evaporated and the residue is purified on 9 g of silicagel Merck in chloroform-acetone 8:2. After crystallisation from ethyl acetate there are obtained colorless crystals of melting point 65°–66°, $[\alpha]_D^{20} = +3° \pm 1°$ (chloroform, c=0.53) representing N-palmitoyl-S-[2(R),3-dihexadecyloxypropyl]-(L)-cysteine.

Using 1-tosyl-[2(S,R),3-dihexadecyl]-glycerine as starting material there is obtained in an analogous manner N-palmitoyl-S[2(R,S),3-dihexadecyloxypropyl]-(L)-cysteine of melting point 87°–88° $[\alpha]_D^{20} = +6° \pm 1°$ (c=0.45 in chloroform).

5.6 g of N-palmitoylcysteine, 5 g of 1,2-epoxy-octadecene and 5.35 g of potassium carbonate in 100 ml ethanol are heated in an atmosphere of nitrogen at 80° for 15 hours. After evaporation, HCl is added so as to obtain a pH of about 3 and the mixture is extracted with chloroform. The chloroform extract is washed with water and is then dried with sodium sulfate. After evaporation there is obtained a colorless residue which is recrystallized from ethyl acetate. There are obtained colorless crystals of the N-palmitoyl-S-[2(R,S)-hydroxyoctadecyl]-(L)-cysteine of melting point 96°–98° $[\alpha]_D^{20} = +16°$ (c=0.78, chloroform).

In an analogous manner starting from N-palmitoyl-(L)-cysteine and 1,2-epoxy-dodecene there is obtained N-palmitoyl-S-[2(S,R)-hydroxydodecyl]-(L)-cysteine of melting point 79°–80° $[\alpha]_D^{20} = +19°$ (c=0.752 in chloroform) and from N-palmitoyl-(L)-cysteine and 1,2-epoxy-eicosene N-palmitoyl-S-[2(S,R)-hydroxyeicosanyl]-(L)-cysteine of melting point 94°–95°; $[\alpha]_D^{20} = +14°$ (c=0.655 in chloroform).

0.2 g of N-palmitoyl-S-[2-(R,S)-palmitoyloxyoctadecyl]-(L)-cysteine benzhydryl ester is dissolved at room temperature in a mixture of 0.4 ml of trifluoroacetic acid and 1.6 ml of methylene chloride and the mixture is allowed to react for 2 hours. The mixture is evaporated to dryness under reduced pressure, the residue is dissolved in chloroform and the chloroform layer is extracted several times with water. After drying with sodium sulfate and evaporation of the solvent there is obtained a crystalline residue, which is dissolved in 2 ml of hot petroleum ether. After addition of 2 ml of ligroin the solution is cooled to −10° and there are obtained crystals of the N-palmitoyloxy-S-[2(R,S)-palmitoyloxyoctadecyl]-(L)-cysteine of melting point 80°–83°.

The starting material can be obtained in the following manner:

0.56 ml of palmitic acid chloride in 5 ml of methylenechloride are added to 0.8 g of N-palmitoyl-S-[2-(R,S)-hydroxyoctadecyl]-(L)-cysteine benzhydryl ester in 5 ml of pyridine. After standing for 24 hours at room temperature the acylation is completed as can be detected by thin layer chromatography on silicagel Merck, chloroform 2 ml of methanol are added and after 20 minutes the reaction mixture is evaporated under reduced pressure. The residue is taken up in chloroform and the chloroform solution is extracted twice each time with 1 N HCl, saturated sodium bicarbonate solution and water, dried over sodium sulfate and evaporated. After purification of the residue over 20 g of silicagel Merck with chloroform as eluant there are obtained colorless crystals of the N-palmitoyl-S-[2(R,S)-palmitoyloxyoctadecyl]-(L)-cysteine-benzhydryl ester, which can be crystallised from acetone-methanol and which melts at 46°–47°.

The benzhydryl ester necessary for the above reaction can be prepared in the following manner:

5.2 g of N-palmitoyl-S[2(R,S)-hydroxyoctadecyl]-(L)-cysteine are dissolved in 60 ml of chloroform-ethanol 1:1 mixture and a solution of 1.93 g of diphenyl-diazomethane in 5 ml of chloroform is added. After 12 hours at room temperature the mixture is evaporated to dryness, the residue is triturated with petroleum ether, then with ligroin and is then recrystallized from ligroin. Colorless crystals of the mentioned ester are obtained melting at 93°–95°.

The following substituted cysteines can be obtained in a manner analogous to that described above:
N-palmitoyl-S[2(R,S)-hydroxydodecyl]-(L)-cysteine
N-palmitoyl-S[2(R,S)-palmitoyloxydodecyl]-(L)-cysteine
N-palmitoyl-S[2(R,S)-hydroxyeicosanyl]-(L)-cysteine
N-palmitoyl-S[2(R,S)-palmitoyloxyeisocanyl]-(L)-cysteine 4.8 g of docosanyl-p-toluenesulfonate and 5 g of potassium carbonate are added to 3.6 g of N-palmitoyl-(L)-cysteine in 50 ml of ethanol. The mixture is heated under stirring and in a nitrogen atmosphere at 80° for 20 hours. After evaporating to dryness the residue is acidified with 1 N HCl so as to obtain a pH of about 3 and then it is distributed between chloroform and water. After having dried and evaporated the chloroform layer a colourless crystalline residue is obtained, which is recrystallized from ethyl acetate. There is thus obtained the N-palmitoyl-S-docosanyl-(L)-cysteine.

N-palmitoyl-(L)-cysteine is reacted in an analogous manner with 1-bromo-octadecane and N-palmitoyl-S-octadecyl-(L)-cysteine of melting point 90°–92° is thus obtained; $[\alpha]_D^{20} = +13°$ (c=1.33 chloroform).

N-palmitoyl-S-dodecyl-(L)-cysteine is obtained in the same manner.

N-palmitoyl-S-[cholesteryl-(3)]-(L)-cysteine is obtained from N-palmitoyl-(L)-cysteine and cholesteryl-p-toluenesulfonate.

N-palmitoyl-S-(3,6-dioxadocosanyl)-(L)-cysteine is obtained from 1-(p-toluenesulfonyl)-diethylene-glycol monocetyl ether and N-palmitoyl-(L)-cysteine.

From the p-toluene sulfonate of retinol (vitamin-A-alcohol) there is obtained in an analogous manner N-palmitoyl-S-retinyl-(L)-cysteine, and N-palmitoyl-S-phytyl-(L)-cysteine from the p-toluenesulfonate of phytol.

From farnesylbromide there is obtained in an analogous manner N-palmitoyl-S-farnesyl-(L)-cysteine.

EXAMPLE 23

The following substituted cysteines
$Cys_1$ = N-Palmitoyl-S-[2(R,S-3-dihexadecyloxy-propyl]-(L)-cysteine
$Cys_2$ = N-Palmitoyl-S-[2(R,S)-hydroxydodecyl]-(L)-cysteine
$Cys_3$ = N-Palmitoyl-S-2-hydroxyeicosanyl-(L)-cysteine
$Cys_4$ = N-Palmitoyl-S-[2(R,S)-hydroxydodecyl]-(L)-cysteine
$Cys_5$ = N-Palmitoyl-S-[2(R,S)-palmitoyloxydodecyl](L)-cysteine
$Cys_6$ = N-Palmitoyl-S-[2(R,S)-hydroxy-eicosanyl]-(L)-cysteine
$Cys_7$ = N-Palmitoyl-S-[2(R,S)-palmitoyloxy-eicosanyl]-(L)-cysteine
$Cys_8$ = N-Palmitoyl-S-docosanyl-(L)-cysteine
$Cys_9$ = N-Palmitoyl-S-octadecyl-(L)-cysteine
$Cys_{10}$ = N-Palmitoyl-S-dodecyl-(L)-cysteine
$Cys_{11}$ = N-Palmitoyl-S-[cholesteryl-(3)]-(L)-cysteine
$Cys_{12}$ = N-Palmitoyl-S-(3,6-dioxa-docosanyl)-(L)-cysteine
$Cys_{13}$ = N-Palmitoyl-S-retinyl-(L)-cysteine
$Cys_{14}$ = N-Palmitoyl-S-phytyl-(L)-cysteine
$Cys_{15}$ = N-Palmitoyl-S-farnesyl-(L)-cysteine
are condensed with each of the following peptides according to the method of Example 19
H-Ser-Ser-Phe-Ala-Glu-OH
H-Ser-Ser-D-Asn-Ala-Glu-Oh
H-Thr-Thr-Asn-Ala-Lys-OH
H-Ser-Thr-Asn-D-Ala-Lys-OH
H-Ser-Ser-Asn-Ala-Glu-OH
H-Thr-Ser-Phe-Ala-D-Glu-OH
H-Ser-Ser-Phe-Ala-D-Glu-OH
thereby obtaining the corresponding lipopeptides of the general formula $$Cys_n-X,$$

where X is any of the peptide sequences just mentioned and $Cys_n$ any of the above mentioned substituted cysteine derivatives from $Cys_1$ to $Cys_{14}$.

EXAMPLE 24

N-Palmitoyl-S-[2(R,S),3-dihexadecyloxy-propyl]-(L,D)-homo cysteine 15.3 g of L,D-homocysteine-thiolactone-hydrochloride are dissolved in 150 ml of pyridine and 30 g of palmitic acid chloride in 50 ml of methylene chloride are added dropwise with stirring. After stirring for 15 hours at room temperature the bath is concentrated in vacuo, the residue is taken up in chloroform and is extracted with 2 N hydrochloric acid, then with water. After drying the chloroform layer with sodium sulfate and concentrating, the residue is triturated with hexane, whereby there are obtained crystals of the N-palmitoyl-homo-(L,D)-cysteine-thiolactone.

5 g of this lactone are taken up in 50 ml of ethanol and 0.95 g of (1 equivalent) of KOH (85%) and 5 g of potassium carbonate are added and the whole is heated to 70°. After keeping the batch for 30 minutes at this temperature 10 g (1,04 equivalents) of 1-tosyl-[2,3-dihexadecyl]-glycerine in 20 ml ethanol are added and the whole is allowed to react for 20 hours at 80°. The batch is then evaporated to dryness, acidified with 1 N hydrochloric acid and distributed between chloroform and water. The chloroform layer is dried with sodium sulfate and a syrup is obtained after evaporation, which is purified upon silicagel Merck in chloroform-acetone 1:1. Colorless crystals are obtained after crystallization from ethyl acetate.

N,S-dipalmitoyl-(L)-cysteine 10.5 g of L-cysteine-hydrochloride-hydrate was suspended in a mixture of 100 ml of pyridine and 50 ml of dimethylacetamide. A solution of 17 g (18,7 ml) of palmitic acid chloride in 50 ml of methylene chloride are added dropwise, while stirring thoroughly and under nitrogen. After 25 hours reaction time at room temperature the mixture is concentrated to a syrup under vacuum, 2 N hydrochloric acid is added and the residue is distributed between chloroform and water. The chloroform layer is washed until hydrochloric acid is no longer detectable. After drying and evaporating the chloroform solution a syrup is obtained, which crystallizes upon trituration with hexane. After two crystallizations from acetone colorless crystals of the N,S-dipalmitoyl-(L)-cysteine of melting point 82°–84° are obtained.

EXAMPLE 25

1.5 g of N,S-dipalmitoyl-Cys-Ser(Bu$^t$)-Ser(Bu$^t$)-Asn-Ala-Pro-NH$_2$ are dissolved in 50 ml of 90% trifluoro acetic acid and the solution is evaporated after standing for 45 minutes at room temperature. The residue is dried over potassium hydroxide. The N,S-dipalmitoyl-Cys-Ser-Ser-Asn-Ala-Pro-NH$_2$ is obtain which constitutes a white powder and possesses the Rf-value 0.50 (157 c) in the thin layer chromatogram on silicagel.

The starting compound may be obtained by the methods described in Examples 15–18 from N,S-dipalmitoyl-(L)-cysteine and H-Ser(Bu$^t$)-Ser(Bu$^t$)-Asn-Ala-Pro-NH$_2$. The Rf value in the thin layer chromatogram (chloroform-methanol 9:1) is 0.20

H-Ser(Bu$^t$)-Ser(Bu$^t$)-Asn-Ala-Pro-NH$_2$ [Rf-value in thin layer chromatogram on silicagel (157 c)=0.53] can be obtained in an analogous manner as H-Ser(Bu$^t$)-Ser(Bu$^t$)-Phe-Ala-D-Glu(OBu$^t$)$_2$ as described in Example 18.

EXAMPLE 26

N,S-dipalmitoyl-(L)-cysteine and H-Ser(Bu$^t$)-Ser(Bu$^t$)-Asn-Ala-Val-OCH$_3$ are condensed according to the method described in Example 25 and the N,S-dipalmitoyl-Cys-Ser(Bu$^t$)-Ser(Bu$^t$)-Asn-Ala-Val-OCH$_3$ is obtained [Rf-value in the thin layer chromatogram on silicagel (chloroform-methanol 9:1=0.53]. 0.9 g of this compound are taken up in 10 ml of 90% trifluoroacetic acid and the solution is evaporated after 45 minutes. The residue is digested with petroleum ether, dried over potassium hydroxide. There is obtained the N,S-dipalmitoyl-Cys-Ser-Ser-Asn-Ala-Val-OCH$_3$ as a white powder on evaporation of the solvent. Rf-value in thin layer chromatogram on silicagel=0.6 (157 c).

H-Ser(Bu$^t$)-Ser(Bu$^t$)-Asn-Ala-Val-OCH$_3$ can be obtained in the same manner as H-Ser(Bu$^t$)-Ser(Bu$^t$)-Phe-Ala-D-Glu(OBu$^t$)$_2$ as described in Example 18. [Rf-value in thin layer chromatogram on silicagel=0.43 (157 c].

EXAMPLE 27

1.2 g of N-palmitoyl-S-octadecyl-D-Cys-Ser(Bu$^t$)-Ser-(Bu$^t$)-Phe-Ala-Glu(OBu$^t$)$_2$ are dissolved in 12 ml of 90% trifluoro acetic acid and the solution is allowed to stand at room temperature for 45 minutes, whereupon it is evaporated. The residue is digested with petroleum ether and the solution dried over potassium hydroxide. N-palmitoyl-S-octadecyl-D-Cys-Ser-Ser-Phe-Ala-Glu OH is obtained as a white powder. Rf-value in thin layer chromatogram on silicagel=0.38 (157 c).

The starting compound may be obtained according to the methods described in the Examples 15–18 from N-palmitoyl-S-octadecyl-D-cysteine and H-Ser(Bu$^t$)-Ser(Bu$^t$)-Phe-Ala-Glu(OBu$^t$)$_2$. Rf-value in thin layer chromatogram=0.70 (157 a).

EXAMPLE 28

0.95 g of N-palmitoyl-S-octadecyl-(L,D)-homocysteinyl-Ser(Bu$^t$)-Ser(Bu$^t$)-Phe-Ala-Glu(OBu$^t$)$_2$ are added to 10 ml of 90% trifluoro acetic acid and the solution is evaporated after standing for 40 minutes. The residue is digested with ethyl acetate and dried over potassium hydroxide. There is obtained N-palmitoyl-S-octadecyl-(L,D)-homocysteinyl-Ser-Ser-Phe-Ala-Glu-OH as a white powder. The Rf-value in the thin layer chromatogram on silicagel is 0.42 (157 c).

The starting compound can be obtained following the method described in Examples 15–18 starting from N-palmitoyl-S-octadecyl-(L,D)-homocysteine and H-Ser(Bu$^t$)-Ser(Bu$^t$)-Phe-Ala-Glu(OBu$^t$)$_2$. The Rf-value in the thin layer chromatogram on silicagel is 0.75 (157 a).

EXAMPLE 29

1.1 g of N-palmitoyl-S-farnesyl-Cys-Ser(Bu$^t$)-Ser(Bu$^t$)-Phe-Ala-Glu(OBu$^t$)$_2$ are added to 10 ml of 90% trifluoro acetic acid. The solution is evaporated to dryness after 40 minutes standing. The residue is digested with petroleum ether and dried over potassium hydroxide. N-palmitoyl-S-farnesyl-Cys-Ser-Ser-Phe-Ala-Glu-OH is obtained as a white powder. The Rf-value in the thin layer chromatogram on silicagel is 0.35 (157 c).

The starting compound may be obtained by the method described in Examples 15–18 from N-palmitoyl-S-farnesyl-(L)-cysteine and H-Ser(Bu$^t$)-Ser(Bu$^t$)-Phe-Ala-Glu(OBu$^t$)$_2$.

EXAMPLE 30

If each of the N-palmitoyl-S-octadecyl-(D)-cysteine, N-palmitoyl-S-octadecyl-(L,D)-homocysteine and N-palmitoyl-S-farnsesyl-(L)-cysteine mentioned in Examples 27 to 29, and which will be identified hereafter by the designations C$_8$OH, C$_9$OH and C$_{10}$OH respectively, the OH group indicating the hydroxyl group of the free carboxyl function, is condensed with the peptides below, using the same protecting groups as in Examples 15–18 and using the same method
H-Ser-Ser-Asn-Ala-Glu-OH
H-Ser-Ser-Asn-Ala-D-Glu-OH
H-Thr-Ser-Phe-Ala-L-Glu-OH
H-Ser-Ser-D-Phe-Ala-Glu-OH
the following lipopeptides are obtained
C$_8$-Ser-Ser-Asn-Ala-Glu-OH
C$_8$-Ser-Ser-Asn-Ala-D-Glu-OH
C$_8$-Thr-Ser-Phe-Ala-Glu-OH
C$_8$-Ser-Ser-D-Phe-Ala-Glu-OH
C$_9$-Ser-Ser-Asn-Ala-Glu-OH
C$_9$-Ser-Ser-Asn-Ala-D-Glu-OH
C$_9$-Thr-Ser-Phe-Ala-Glu-OH
C$_9$-Ser-Ser-D-Phe-Ala-Glu-OH
C$_{10}$-Ser-Ser-Asn-Ala-Glu-OH
C$_{10}$-Ser-Ser-Asn-Ala-D-Glu-OH
C$_{10}$-Thr-Ser-Phe-Ala-Glu-OH
C$_{10}$-Ser-Ser-D-Phe-Ala-Glu-OH.

EXAMPLE 31

5 g (13.9 mMol) of N-palmitoyl-(L)-cysteine and 4.76 g (16.7 mMol=1,2 equ.) of farnesyl bromide are dissolved in 50 ml of ethanol. 4.8 g of potassium carbonate are added, after cooling to 25°, and the solution is heated 9 hours at about 60° in an atmoshere of nitrogen. 5 ml of ethanol are then added and the solution is further heated for 6 hours at 70°. It is then evaporated to dryness, the residue is acified with 2 N hydrochlorid acid and then ethyl acetate and water added. The ethyl acetate layer is repeatedly extracted with water in order to remove the mineral acid. After drying and evaporating the organic layer 8.1 g of a syrup are obtained which is purified over silicagel (Merck) with methylene chloride-ethanol 9:1. A yellowish amorphous compound representing N-palmitoyl-S-farnesyl-(L)-cysteine having the Rf-value 0.48 (chloroform-methanol 9:1) in the thin layer chromatogram on silicagel Merck is obtained. $[\alpha]_D^{20} = +2°$ (chloroform, c=0.435).

N-palmitoyl-S-octadecyl-(D)-cysteine may be obtained as follows:

A solution of 360 mg (1mMol) of N-palmitoyl(D)-cysteine in 2 ml of dimethoxyethane is added to 48 mg sodium hydride dispersion (mineral oil) in 1 ml of dimethoxyethane in an atmosphere of nitrogen. After stirring for 20 minutes 400 mg of 1-bromo-octadecane (1.2 mMol) in 4 ml of dimethoxyethane are added to the said suspension. The batch is kept for 15 hours under thorough stirring in a nitrogen atmosphere at 80°. It is then evaporated to dryness, taken up in chloroform and acidified with 1 N hydrochloric acid. Chloroform and aqueous hydrochloric acid are then added, the chloroform layer is then repeatedly washed with water, dried with sodium sulfate and evaporated in vacuo. 600 mg of a slightly yellowish crystalline powder are obtained, which are purified on silicagel with chloroform-ethanol 9:1.

Colorless crystals of N-palmitoyl-S-octadecyl-(D)-cysteine having an Rf-value of 0.55 (thin layer on silicagel Merck-chloroform-methanol 9:1) and a melting point of 100°-102°, are obtained, $[\alpha]_D^{20} = -12°$ (chloroform).

N-palmitoyl-S-octadecyl-(L,D)-homocysteine may be obtained as follows:

5.1 ml of 4 N sodium hydroxide are added in a nitrogen atmosphere to 3.55 g (0.01 Mol) of N-palmitoyl-(L,D)-homocysteine-thiolactone in 40 ml of ethanol-dioxane 2:1. After stirring for 20 minutes 3.76 g (0,012 Mol) of octadecylbromide are added and the whole is heated for 12 hours at 80° in a nitrogen atmosphere. The mixture is then evaporated to dryness in vacuo and acidified with 2 N hydrochloric acid. Chloroform and water are then added, the organic layer is then dried with sodium sulfate and the above named compound is obtained after evaporation as a colorless compound of Rf-value 0.6 (thin layer chromatogram on silicagel Merck-chloroform-ethanol 9:1); melting point 100°-105°, after crystallisation from ethyl acetate.

EXAMPLE 32

A suitable pharmaceutical form for parenteral administration, preferably subcutaneous administration, of the lipopeptides according to this invention is prepared in the following manner:

3 mg of the lipopeptide according to Example 3 {N-palmitoyl-S-[2(R),3-di-palmitoyloxypropyl]-Cys-Ser-Ser-Phe-Ala-Glu-OH} are dissolved together with 27 mg of lecithin in a mixture of chloroform and methanol 2:1. The mixture is then concentrated in a rotary evaporator under vacuum so as to obtain a lipid film. A 0,2 ml of a sterile pyrogen-free 0.9% NaCl-solution "Flec-Flac" of the firm VIFOR S.A., Geneva, are added. The batch is irradiated acoustically for about 2 minutes at room temperature and a suspension of lecithin-particles (liposomes) are thus obtained having a diameter of about 1 to 5μ including the lipopeptide. This suspension is e.g. administered subcutaneously or intraperitoneally to the mouse in doses of 0.1 ml per 10 g animal.

Similar pharmaceutical preparation for administration to humans can be manufactured in an analogous manner.

EXAMPLE 33

0.8 g of N-palmitoyl-S-(3,6,9,12,15,18,21,24,27-nonaoxa-octacosanyl)-Cys-Ser(Bu$^t$)-Ser(Bu$^t$)-Phe-Ala-Glu(OBu$^t$)$_2$ are dissolved in 10 ml of 90% trifluoroacetic acid and the solution is evaporated after standing for 40 minutes at room temperature. The residue is digested with ethyl acetate and then dried over potassium hydroxide. There is thus obtained the N-palmitoyl-S-(3,6,9,12,15,18-21,24,27-nonaoxa-octadosanyl)-Cys-Ser-Ser-Phe-Ala-Glu-OH as a white powder. The Rf-value in thin layer chromatography on Silicagel is 0.29 (157 c).

The starting material may be obtained following the method described in Examples 1-4 from N-palmitoyl-S-(3,6,9,12,15,18,21,24,27-nonaoxa-octacosanyl)-cysteine and H-Ser(Bu$^t$)-Ser(Bu$^t$)-Phe-Ala-Glu (OBu$^t$)$_2$.

N-palmitoyl-S-(3,6,9,12,15,18,21,24,27-nonaoxa-octosanyl)-(L)-cysteine can be obtained in the following manner:

1 g of 1-bromo-3,6,9,12,15,18,21,24,27-nonaoxa-octacosane (bromide of nonaethylene glycol-monomethyl ether), 0.61 g of N-palmitoyl-(L)-cysteine and 0.6 g of potassium carbonate in 13 ml of ethanol are heated for 15 hours in a nitrogen atmosphere at 80°. The batch is then evaporated to dryness in vacuo, the residue is taken up in chloroform and this solution is washed once with 2 N hydrochloric acid and 3 times with water. After drying the chloroform layer here are obtained 1.2 g of the above named compound upon evaporation as a syrup which is purified on silicagel Merck using chloroform-methanol 9:1. The pure fractions are united and the solvent evaporated, giving a colorless syrup. Rf-value=0.5 in the thin layer chromatogram on silicagel Merck-chloroform-methanol=8:2.

The bromide of the nonaethylenglycol monomethyl-ether may be obtained from 10 g of nonaethyleneglycol-monomethyl ether, 0.87 ml of phosphorus tribromide and 0.44 ml of absolute pyridine in 6 ml of ether. These compounds are mixed at a temperature between −10° and −5°, and the mixture is then stirred for 16 hours at room temperature. 30 ml of a mixture of chloroform and ether 1:1 are then added, the undissolved part is filtered off and the filtrate is evaporated in vacuo so as to obtain an oil. The compound is used direct for the next stage.

What we claim:

1. Compounds of the formula

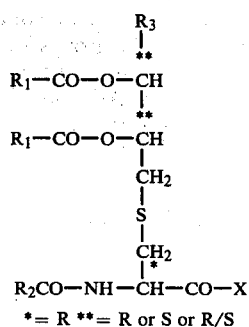

(I)

\* = R  \*\* = R or S or R/S wherein $R_1$ and $R_2$ each represent a saturated or unsaturated aliphatic or mixed aliphatic-cycloaliphatic hydrocarbon radical which has 11–21 C atoms and which is unsubstituted or substituted by hydroxyl or epoxy, $R_3$ represents hydrogen or the radical $R_1$—CO—O—$CH_2$—, where $R_1$ has the same meaning, and X represents an amino acid $X_1$ or a sequence of 5 amino acids selected from the groups $X_1$–$X_5$, wherein $X_1$ is selected from the group consisting of Ser, Phe, Glu, Val, Ala, Thr, D-Ser, D-Thr, Gln, Asn and Asp, $X_2$ is selected from the group consisting of Ser, Phe, Glu, Ile, Lys, Thr, D-Ser, D-Phe, Gln, Asn and Asp, $X_3$ is selected from the group consisting of Phe, Asn, Ile, Val, Gly, Ala, Tyr, D-Asn, D-Phe and D-Ala, $X_4$ is selected from the group consisting of Ala, Phe, Tyr, Val, Glu, D-Glu and D-Ala and $X_5$ is selected from the group consisting of Glu, Lys, Ala, Pro, D-Glu and Val, or X represents a sequence of amino acids resulting from the addition of any of the series Asp-Glu, Ala-Pro or -Ile-Asp-Glu to said 5 membered series, with the proviso that the amino acid $X_1$ and the sequence $X_1$–$X_5$ is different from Ser or any of the series -Ser-Ser-Asn-Ala-Lys, -Ser-Ser-Asn-Ala, -Ser-Ser-Asn and -Ser-Ser, respectively, in compounds of formula (I), the terminal carboxyl group being in the free form or the form of the amide or a substituted amide having one or two alkyl groups with 1–7 C atoms or in the form of an ester group having from 1 to 7 C atoms, the amino acids being natural ones in the case of compounds of formula (I), and to diastereomeric mixtures and salts of said compounds.

2. Compounds of formula (I) according to claim 1 wherein the acyl groups $R_1$CO are derived from saturated or unsaturated fatty acids having 14–18 C atoms.

3. Compounds of formula (I) according to claim 1, wherein the acyl groups are derived from palmitic, stearic, oleic, lauric, myristic, behenic, dihydrosterculic, malvalic, hydnocarpic or chaulmoogric acid.

4. Compounds according to claim 1, of the formula

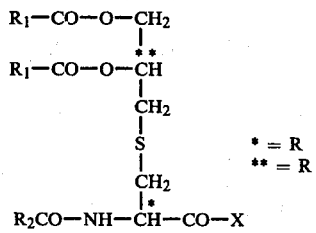

\* = R
\*\* = R wherein in a peptide chain X at least half of the amino acids have a hydrophilic group, and salts thereof.

5. Compounds according to claim 4, wherein X represents one of the following peptide sequences:
-Thr-Thr-Asn-Ala-Lys-OH
-Thr-Thr-Asn-Ala-OH
-Thr-Thr-Asn-OH
-Thr-Thr-OH,
-Asn-Asn-Asn-Ala-Lys-OH
-Asn-Asn-Asn-Ala-OH
-Asn-Asn-Asn-OH
-Asn-Asn-OH,
-Gln-Gln-Asn-Ala-Lys-OH
-Gln-Gln-Asn-Ala-OH
-Gln-Gln-Asn-OH
-Gln-Gln-OH, or
-Ser-Ser-Asn-Ala-Glu-OH
-Ser-Ser-Phe-Ala-Glu-OH
-Ser-Ser-Phe-Ala-OH
-Ser-Ser-Phe-OH or sequences of this type in which threonine, glutamine or asparagine are present as exchange amino acids for serine.

6. Compounds according to claim 1, of the formula

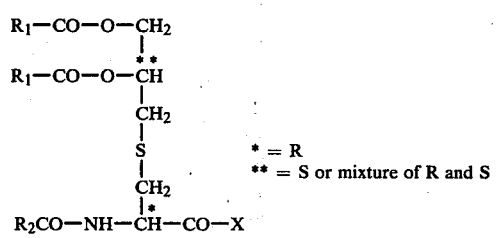

\* = R
\*\* = S or mixture of R and S wherein in a peptide chain X at least half of the amino acids have a hydrophilic group and salts thereof.

7. A lipopeptide as claimed in claim 1 selected from the group consisting of
N-palmitoyl-S-[2(R),3-dipalmitoyloxypropyl]-Cys-Ser-Ser-Phe-Ala-Glu-OH,
N-palmitoyl-S-[2(R,S),3-dipalmitoyloxypropyl]-Cys-Phe-Phe-Asn-Ala-Lys-OH,
N-myristoyl-S-[2(R),-3-dipalmitoyloxypropyl]-Cys-Glu-Gln-Asn-Ala-Lys-OH,
N-lauroyl-S-[2(R),3-dipalmitoyloxypropyl]-Cys-Ser-Ser-Asn-Ala-Glu-OH and
N-stearoyl-S-[2(R),3-dipalmitoyloxypropyl]-Cys-Ser-Ser-Asn-Ala-Ala-OH.

8. A lipopeptide according to claim 1 selected from the group consisting of
N-palmitoyl-S-[2(R),3-diacyloxypropyl]-Cys-Ser-Ser-Phe-Ala-Glu-OH,
N-palmitoyl-S-[2(R,S),3-diacyloxypropyl]-Cys-Phe-Phe-Asn-Ala-Lys-OH, N-myristoyl-S-[2(R),3-diacyloxypropyl]-Cys-Glu-Gln-Asn-Ala-Lys-OH, N-lauroyl-S-[2(R),3-diacyloxypropyl]-Cys-Ser-Ser-Asn-Ala-Glu-OH and N-stearoyl-S-[2(R),3-diacyloxypropyl]-Cys-Ser-Ser-Asn-Ala-Ala-OH in which lipopeptide there are present, as acyl groups in the diacyloxypropyl group lauroyl, stearoyl, oleoyl, behenoyl or dihydrosterculoyl.

9. A lipopeptide as claimed in claim 1 selected from the group consisting of

N-stearoyl-S-[2(R),3-dipalmitoyloxypropyl]-Cys-Ser-Ser-Asn-Ala-Glu-Ile-Asp-Glu-OH, N-palmitoyl-S-[2(R),3(R),4-tripalmitoyloxybutyl]-Cys-Ser-Ser-Asn-Ala-Lys-Ile-Asp-Glu-OH, N-palmitoyl-S-[2(R),3-dipalmitoyloxypropyl]-Cys-Phe-Ile-Ile-Phe-Ala-OH, N-palmitoyl-S-[2(R),3-dipalmitoyloxypropyl]-Cys-Val-Lys-Val-Tyr-Pro-OH, N-palmitoyl-S-[2(R),3-dipalmitoyloxypropyl]-Cys-Ala-Ile-Gly-Val-Gly-Ala-Pro-NH$_2$, and N-palmitoyl-S-[2(R),3-dipalmitoyloxypropyl]-Cys-Ser-Ser-Asn-Ala-Lys-Ile-Asp-Glu-OH, and epimers thereof with a corresponding S-configuration on the C$_2$ atom of the propyl group.

10. An ammonium salt or alkali metal salt or alkaline-earth metal salt of basic compounds and a pharmaceutically applicable, nontoxic acid addition salt of any acid compound according to claim 1.

11. A lipopeptide as claimed in claim 1, and being the N-palmitoyl-S-[2(R),3-dipalmitoyloxypropyl]-Cys-Ser-Ser-Phe-Ala-D-Glu-OH.

12. Compounds of the formula (I) according to claim 1, where X represents an amino acid X$_1$ or a sequence of 5 amino acids selected from the groups X$_1$-X$_5$, wherein X$_1$ is selected from the group consisting of Ser, Phe, Glu, Val, Ala, Thr, Gln, Asn and Asp, X$_2$ is selected from the group consisting of Ser, Phe, Glu, Ile, Lys, Thr, Gln, Asn and Asp, X$_3$ is selected from the group consisting of Phe, Asn, Ile, Val, Gly, Ala and Tyr, X$_4$ is selected from the group consisting of Ala, Phe, Tyr, Val and Glu, and X$_5$ is selected from the group consisting of Glu, Lys, Ala, Pro and Val, or X represents a sequence of amino acids resulting from the addition of any of the series Asp-Glu, Ala-Pro or Ile-Asp-Glu to said 5 membered series, with the proviso that the amino acid X$_1$ and the sequence X$_1$-X$_5$ is different from Ser or any of the series Ser-Ser-Asn-Ala-Lys, -Ser-Ser-Asn-Ala, -Ser-Ser-Asn, or -Ser-Ser, respectively, the terminal carboxyl group being in the free form or in the form of the amide or a substituted amide having one or two alkyl groups with 1–7 C atoms or in the form of an ester group having from 1 to 7 C atoms, and to diastereomeric mixtures of these compounds, and to salts thereof.

13. A pharmaceutical preparation for parenteral administration to warm-blooded animals containing an immunopotentiatingly effective dose of a compound according to claim 12 together with more than 5% of a pharmaceutical carrier.

14. Method of stimulating the immune system of warm-blooded animals said method comprising administering to a warm-blooded animal in need of such treatment an effective dose of a compound according to claim 12.

* * * * *

UNITED STATES PATENT AND TRADEMARK OFFICE
CERTIFICATE OF CORRECTION

PATENT NO. : 4,439,425

DATED : March 27, 1984

INVENTOR(S) : Lajos Tarcsay, Bruno Kamber, Jaroslav Stanek, Gerhard Baschang, and Albert Hartmann It is certified that error appears in the above-identified patent and that said Letters Patent is hereby corrected as shown below:

On the cover page, Item 63, Line 6 should read--

Jun. 15, 1978, abandoned --.

On the cover page, Item 30, Line 2 should read--

Dec. 20, 1978 [CH] Switzerland............. 12942/78 --.

Signed and Sealed this

Fifteenth Day of October 1985

[SEAL]

Attest:

Attesting Officer

DONALD J. QUIGG

Commissioner of Patents and Trademarks—Designate